United States Patent
Chuang et al.

(10) Patent No.: US 10,016,365 B2
(45) Date of Patent: Jul. 10, 2018

(54) COMPOSITIONS AND METHODS OF TUMOR TREATMENT UTILIZING NANOPARTICLES

(71) Applicants: OP NANO CO., LTD., Taipei (TW); TRENDMED CO., LTD., Taipei (TW)

(72) Inventors: Chi-Mu Chuang, Taipei (TW); Chi-Tai Chang, Taipei (TW)

(73) Assignees: OP NANO CO., LTD., Taipei (TW); TRENDMED CO., LTD., Beitou Dist., Taipei (TW)

( * ) Notice: Subject to any disclaimer, the term of this patent is extended or adjusted under 35 U.S.C. 154(b) by 0 days.

(21) Appl. No.: 15/550,786

(22) PCT Filed: Feb. 12, 2016

(86) PCT No.: PCT/US2016/017883
§ 371 (c)(1),
(2) Date: Aug. 13, 2017

(87) PCT Pub. No.: WO2016/131006
PCT Pub. Date: Aug. 18, 2016

(65) Prior Publication Data
US 2018/0028444 A1    Feb. 1, 2018

Related U.S. Application Data

(60) Provisional application No. 62/115,635, filed on Feb. 13, 2015.

(51) Int. Cl.
| | | |
|---|---|---|
| *A61K 9/127* | (2006.01) | |
| *A61P 35/00* | (2006.01) | |
| *A61K 31/337* | (2006.01) | |
| *A61K 47/34* | (2017.01) | |
| *A61K 9/107* | (2006.01) | |
| *A61K 9/00* | (2006.01) | |

(52) U.S. Cl.
CPC ............ *A61K 9/127* (2013.01); *A61K 9/0019* (2013.01); *A61K 9/1075* (2013.01); *A61K 31/337* (2013.01); *A61K 47/34* (2013.01); *A61P 35/00* (2018.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

2014/0212479 A1* 7/2014 Zeinelden ............... A61K 9/127
                                                                424/450

OTHER PUBLICATIONS

H Cho, TC Lai, GS Kwon. "Poly(ethylene glycol)-block-poly(ε-caprolactone) micelles for combination drug delivery: Evaluation of paclitaxel, cyclopamine and gossypol in intraperitoneal xenograft models of ovarian cancer." Journal of Controlled Release, vol. 166, pp. 1-9. (Year: 2013).*
S Dadashzadeh, N Mirahmadi, MH Babaei, AM Vali. "Peritoneal retention of liposomes: Effects of lipid composition, PEG coating and liposome charge." Journal of Controlled Release, vol. 148, 2010, pp. 177-186. (Year: 2010).*
R Perez-Solear, DM Shin, SH Siddik, WK Murphy, M Huber, JS Lee, AR Kohkhar, WK Hong. "Phase I Clinical and Pharmacological Study of Liposome-entrapped NDDP Administered Intrapleurally in Patients with Malignant Pleural Effusions." Clinical Cancer Research, vol. 3, Mar. 1997, pp. 373-379. (Year: 1997).*

* cited by examiner

*Primary Examiner* — Isaac Shomer
(74) *Attorney, Agent, or Firm* — Chang-Hsing Liang

(57) ABSTRACT

The present invention is directed to a method for treating cancer intraperitoneally in a subject. The method comprises administering to said subject in need thereof an anti-cancer agent encapsulated in nanoparticles wherein nanoparticles are characterized to slowly release anti-cancer agent in a timely fashion that allows efficient killing of tumor cells. The nanoparticles described herein are characterized to slowly release anti-cancer agent at a rate of 30% or less per 24 hours based on in vitro drug dissolution study.

10 Claims, 59 Drawing Sheets

FIG. 1D
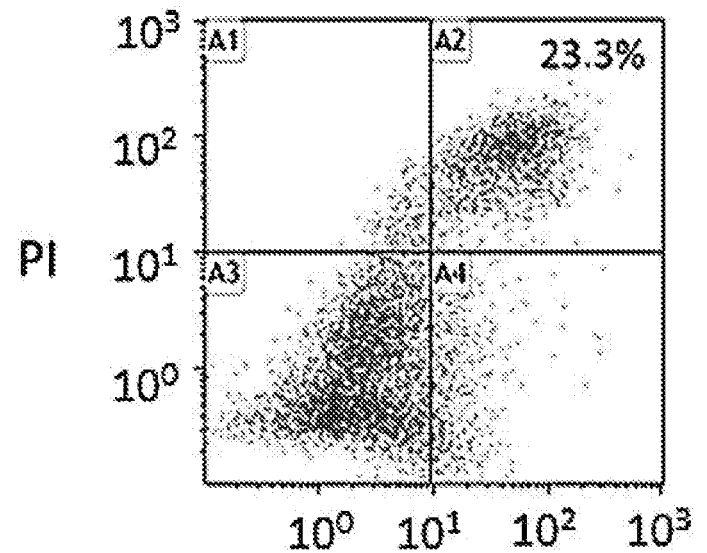
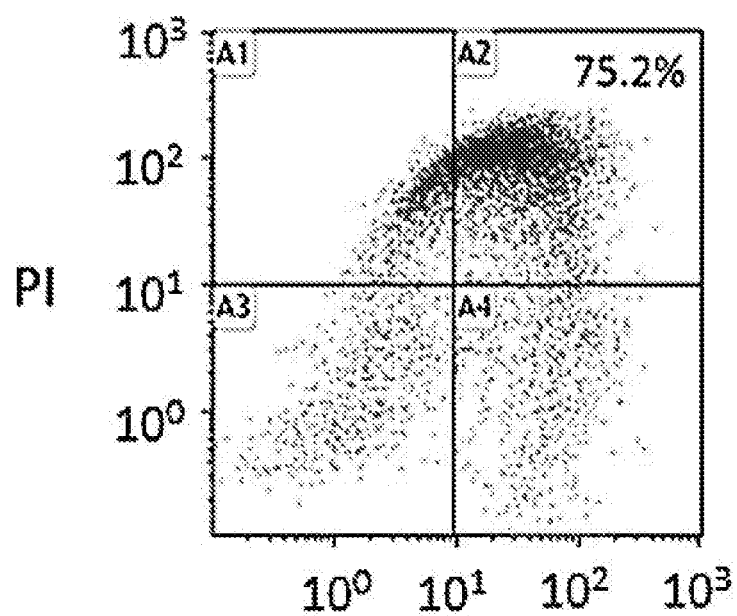

Cisplatin: 5 mg/Kg/Treat

Nano-Platin: 5 mg/Kg/Treat

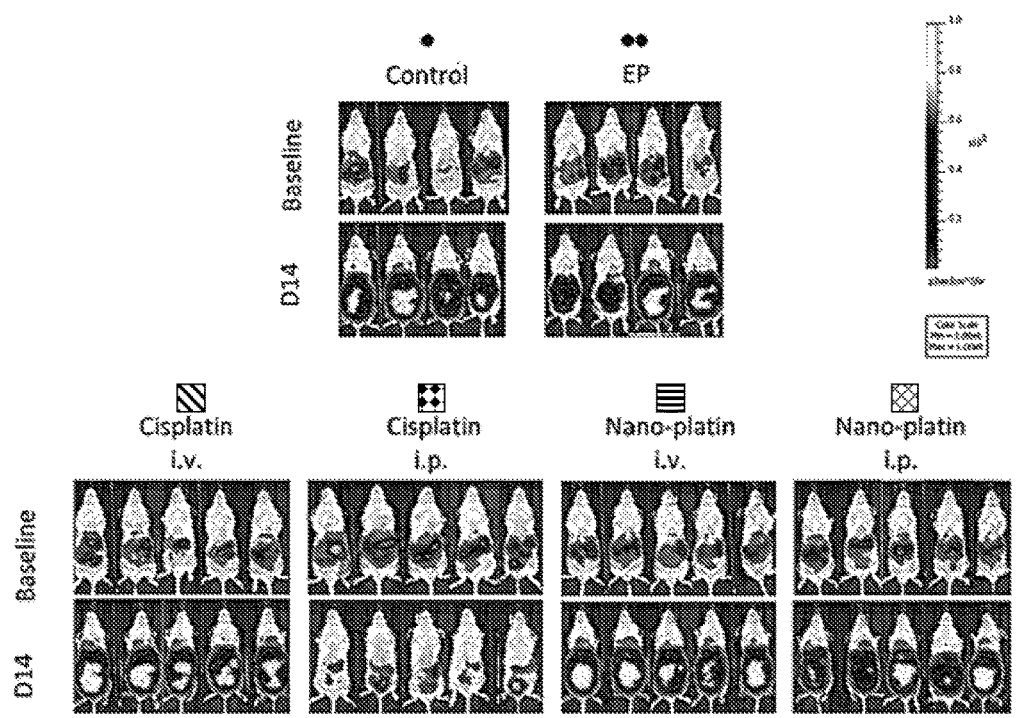

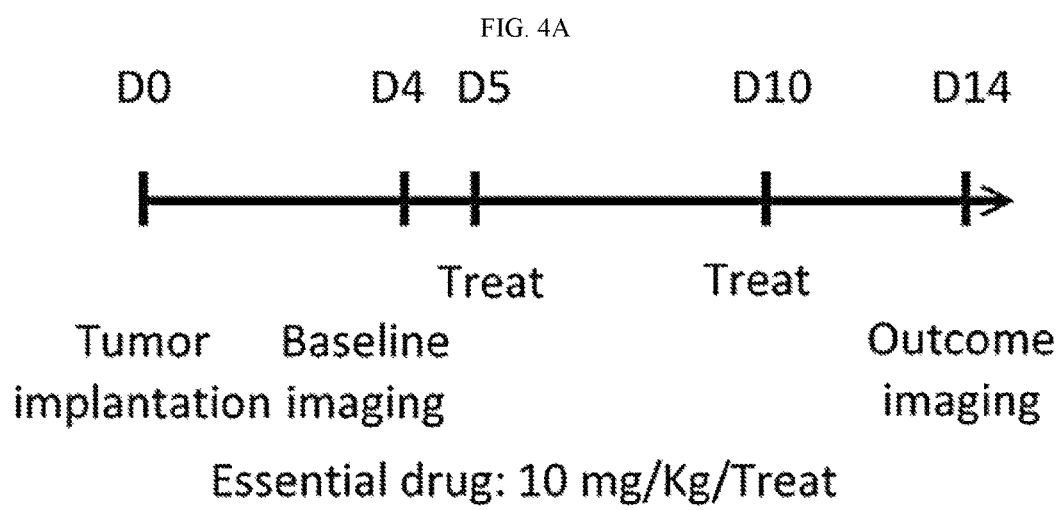

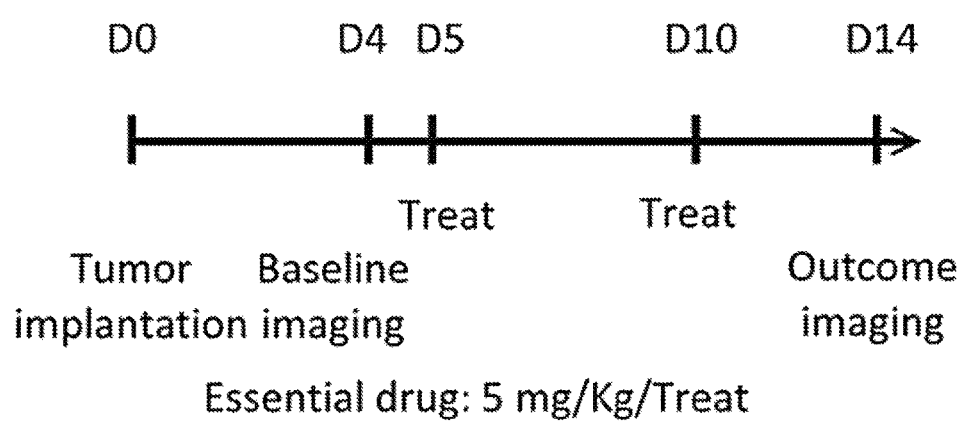

Essential drug: 10 mg/Kg/Treat

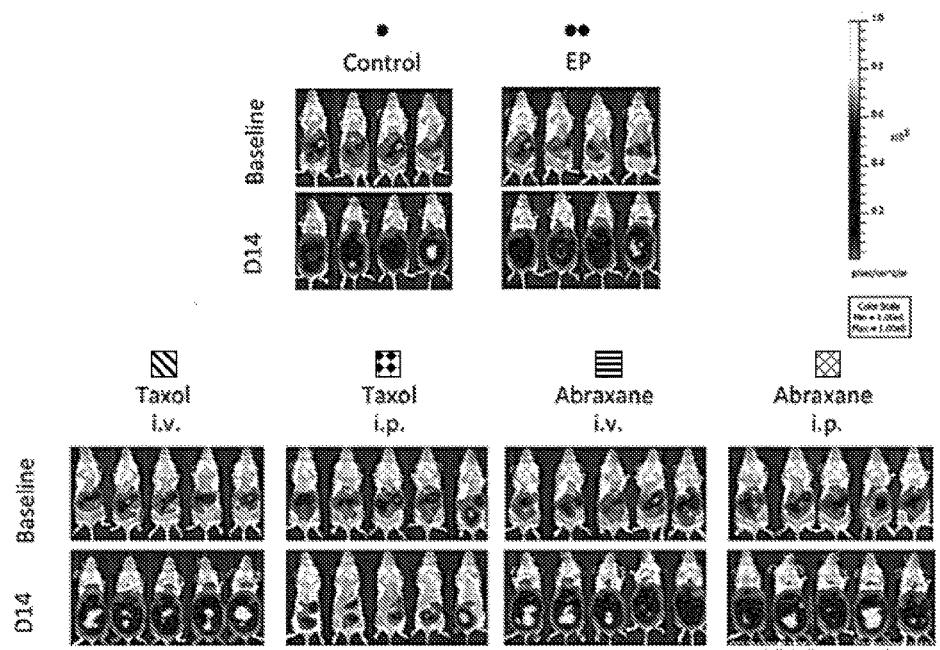

FIG. 7C
   
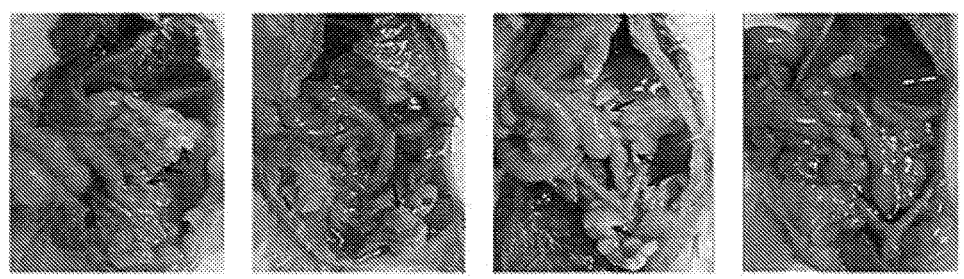
←——— Retroperitoneal lymphatic ———→
metastases

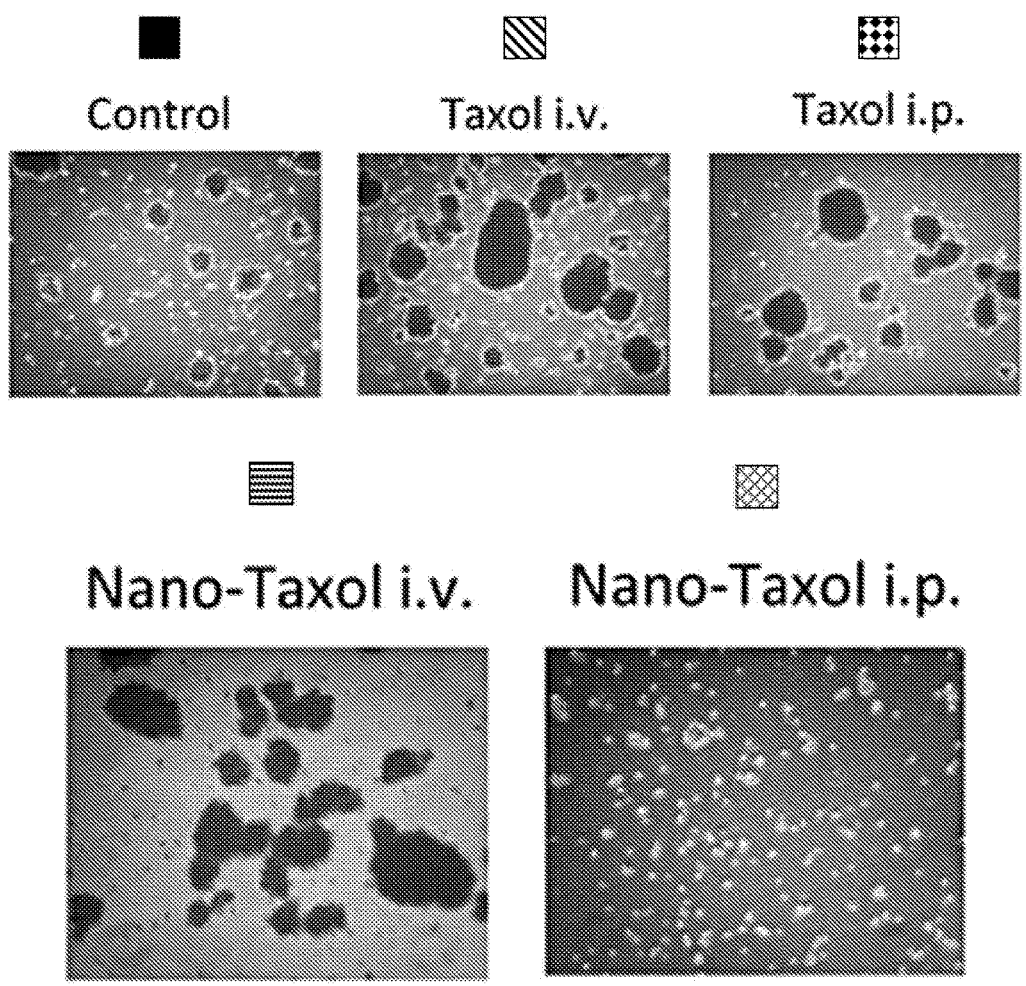

|  | Bowel obstruction | Bowel perforation |
|---|---|---|
| HIPEC (n = 6) | 1 | 1 |
| i.p. Nano-Taxol (n = 6) | 0 | 0 |

FIG. 11
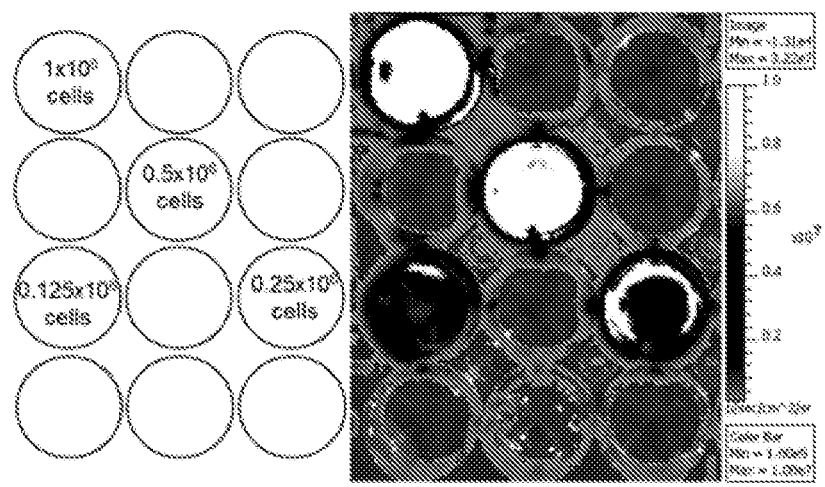
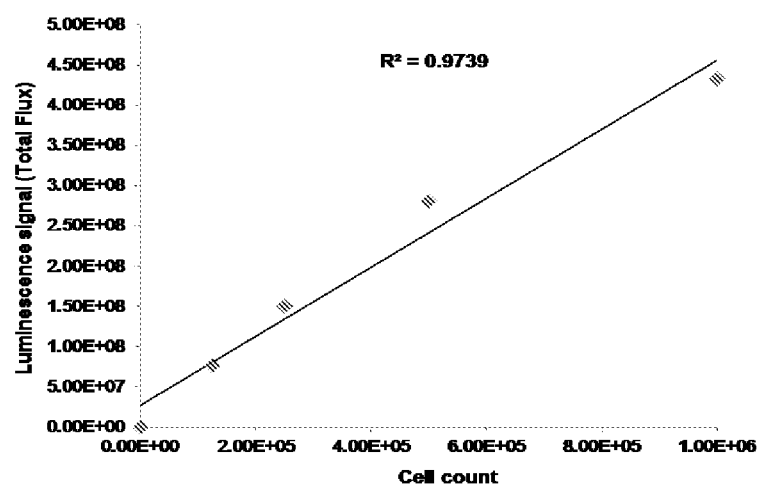

FIG. 12A-B
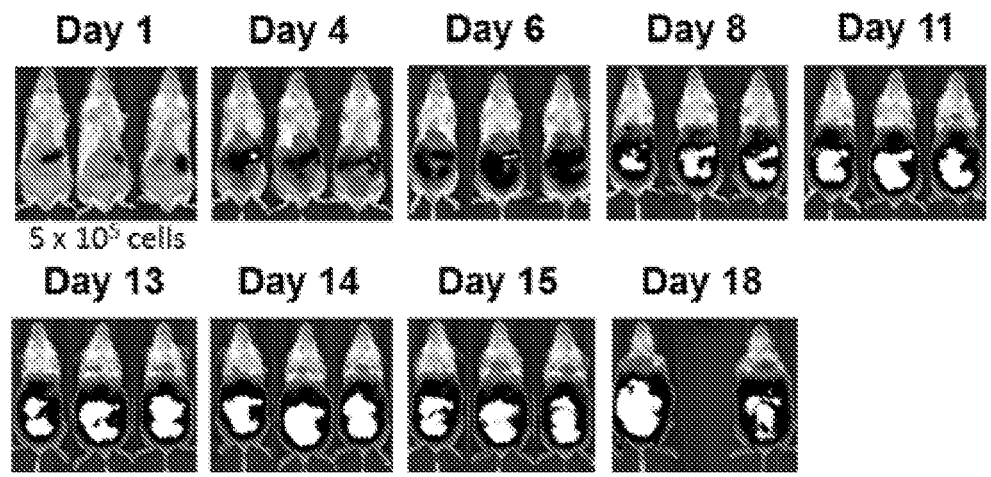
12A
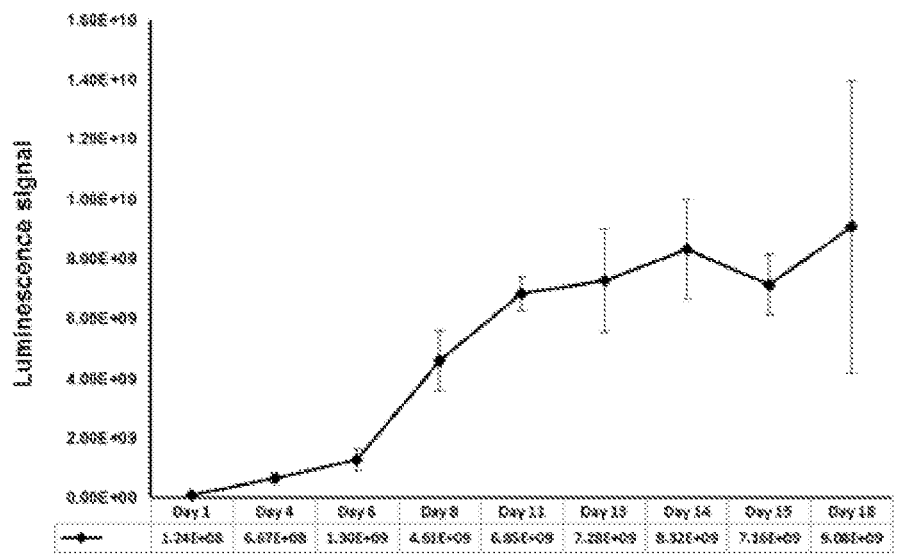
12B

FIG 15A-B
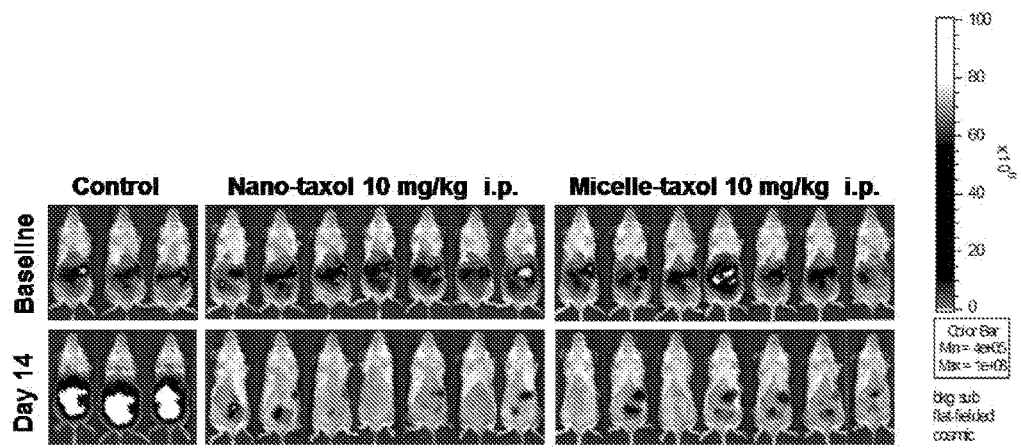
15A
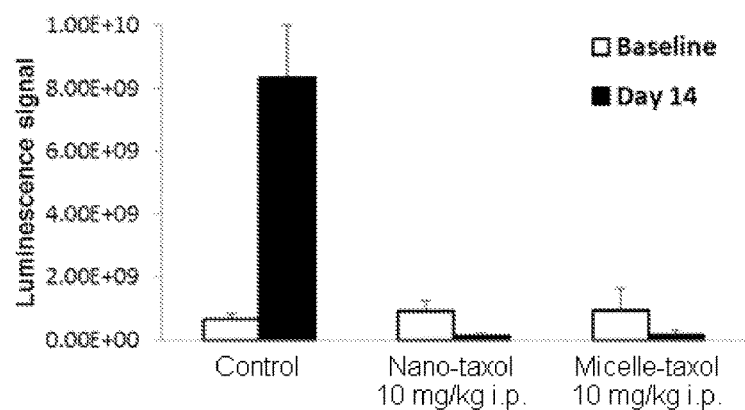
15B

FIG. 16A-G
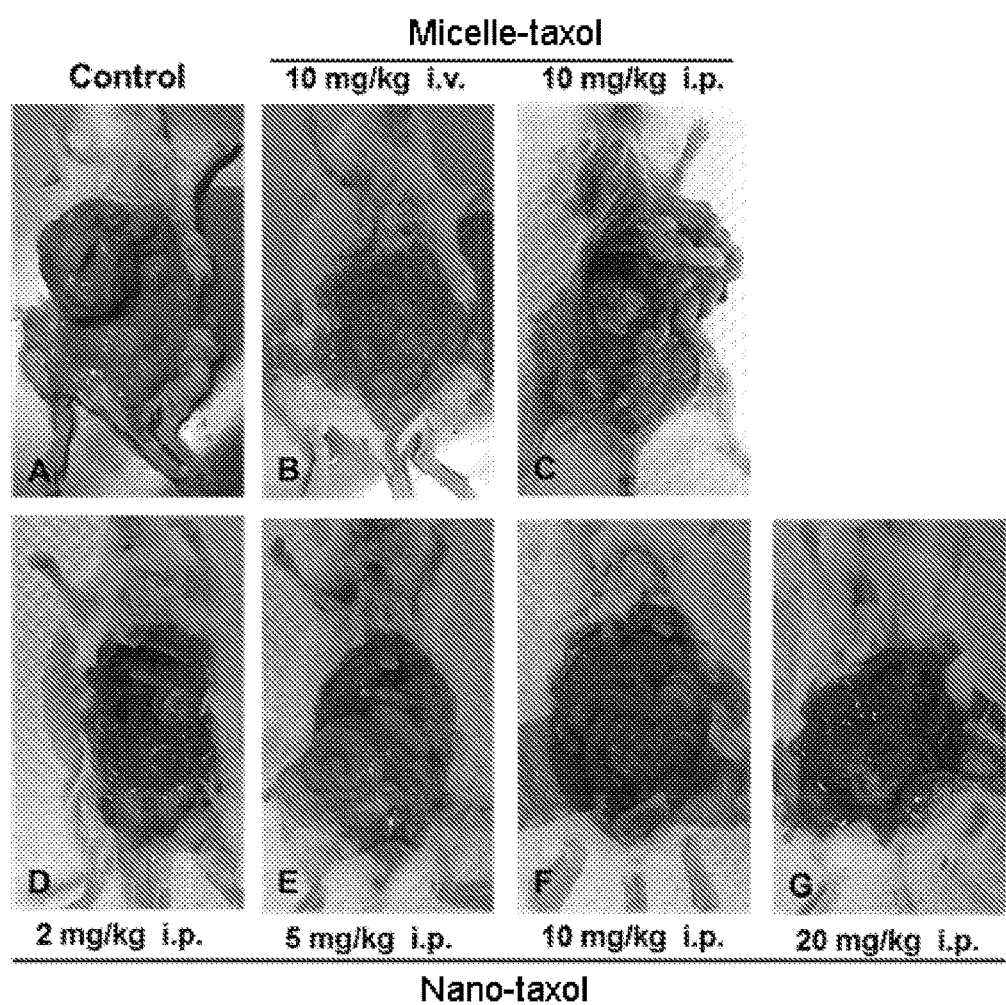

FIG. 22A-B
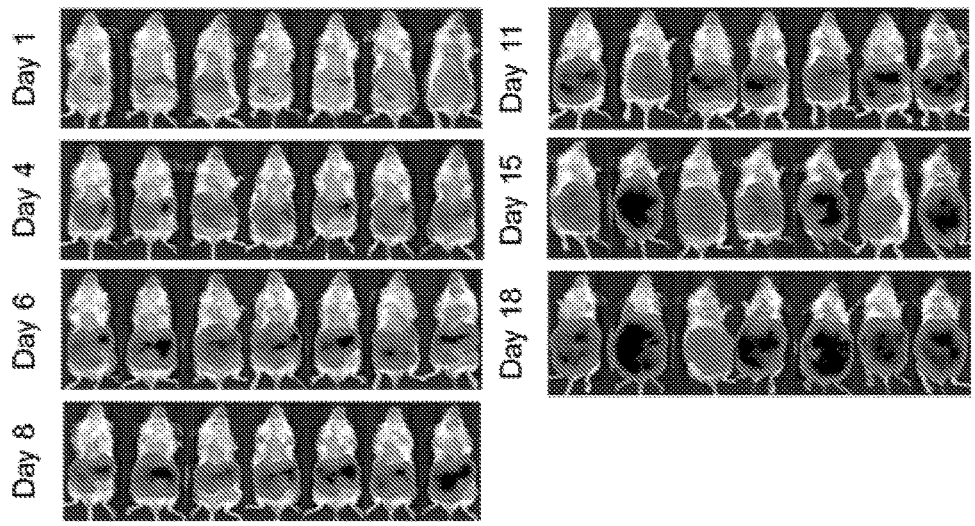
22A
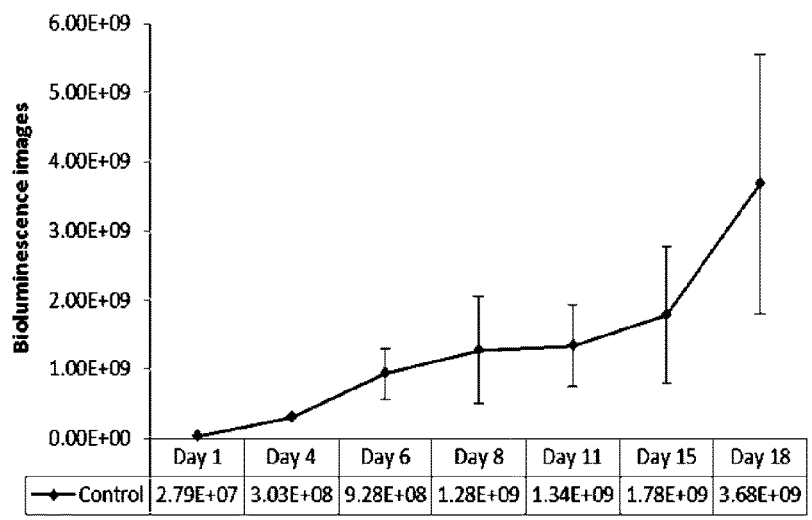
22B

COMPOSITIONS AND METHODS OF TUMOR TREATMENT UTILIZING NANOPARTICLES

BACKGROUND OF THE INVENTION

Ovarian cancer is a cancerous growth arising from the ovary. Most (more than 90%) ovarian cancers are classified as "epithelial" and are believed to arise from the surface (epithelium) of the ovary. However, some evidence suggests that the fallopian tube could also be the source of some ovarian cancers. Since the ovaries and tubes are closely related to each other, it is thought that these fallopian cancer cells can mimic ovarian cancer. Other types may arise from the egg cells (germ cell tumor) or supporting cells. Ovarian cancers are included in the category gynecologic cancer.

Treatment of ovarian cancer usually involves chemotherapy and surgery, and sometimes radiotherapy. Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard.

For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high "drop-out" rate, the group as a whole (including the patients that didn't complete IP chemotherapy treatment) survived longer on average than patients who received intravenous chemotherapy alone. Although IP chemotherapy has been recommended as a standard of care for the first-line treatment of ovarian cancer, the basis for this recommendation has been challenged, and it has not yet become standard treatment for stage III or IV ovarian cancer.

Colon cancer is one of the most common types of cancer. Peritoneal spread is the terminal stage in colon cancer. The peritoneal carcinomatosis is the most common cause of malignant ascites; the production and leakage of fluid from the malignant cells causes exudation of extracellular fluid into peritoneal cavity. Peritoneal carcinomatosis is one of the major causes of mortality in colon cancer patients.

The combination of nanotechnology and conventional chemotherapy has yielded a new therapeutic strategy that is intended to bring critical advances in the fight against cancer. Nanoparticles (NPs), such as liposomes and albumin, currently employed in clinical practice, aim to improve the solubility and efficacy while decreasing the adverse side effects. The enhanced permeability and retention (EPR) effect is becoming the gold standard for the development of nanomedicine.

SUMMARY OF THE INVENTION

In one aspect provided herein are methods for treating cancer intraperitoneally in a subject comprising administering to said subject in need thereof an anti-cancer agent encapsulated in nanoparticles wherein nanoparticles are characterized to slowly release anti-cancer agent in a timely fashion that allows efficient killing of tumor cells.

In another aspect provided herein are methods for treating cancer via regional delivery in a subject comprising administering to said subject in need thereof an anti-cancer agent encapsulated in sustained release nanoparticles wherein the anti-cancer agent nanoparticles are administered intrapleurally.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-1F show exemplary characteristics and synergism of sustained-release liposomal paclitaxel. (1A) The unilamellar morphology of the liposomes was demonstrated by transmission electron microscopy, with the liposomes estimated to have an average size of 100 nm. (1B) Mathematical processing of the in vitro drug dissolution release data showed that the release of paclitaxel from liposomes obeyed the Higuchi release kinetics (square root of time, $R^2=0.9864$) at a rate of 30% or less per 24 hours, indicating a specific diffusion-controlled model. (1C) Intra-tumor drug concentration of Nano-Taxol versus Taxol® by systematic or regional delivery. Regional delivery of Nano-Taxol achieves the highest $AU_{0-\infty}$. (1D) Flow cytometry of apoptosis assay of tumor after regional delivery of Nano-Taxol versus systematic delivery of Taxol, the current standard therapy for ovarian cancer. Apoptosis is significantly higher in the former group (75.2%) then in the latter group (23.3%). (1E) Chou-Talalay plot, a plot of combination index on the y-axis as a function of effect levels (Fa) on the x-axis. The drug combination index of six experimental points are all less than 1, indicating synergistic effect between nanomedicine and regional delivery. (1F) Normalized isobolograms. Values below the threshold line represent synergistic combination. Experiments were repeated in triplicate.

FIG. 3A-D show exemplary therapeutic effects of regional delivery of Nano-platin. (3A) Treatment schema. Both cisplatin and Nano-platin were administered at essential drug 5 mg/kg/mouse per treat. (3B) Evaluation of therapeutic efficacy. Mouse was implanted with ES-2 cells ($2\times10^5$/mouse) at day 1 and was treated at day 5 and day 10 at indicated dosage. Bioluminescence imaging was captured at day 4 (baseline) and at day 14. Regional delivery of cisplatin shows some therapeutic effect. However, regional delivery of Nano-platin demonstrated almost no therapeutic effect. (3C) Hazard ratio of overall survival in each group. (3D) White cell count in each group. Experiments were repeated in triplicate.

FIG. 4A-D show exemplary therapeutic effects of regional delivery of Nano-topotecan. (4A) Treatment schema. Both topotecan and Nano-topotecan were administered at essential drug 10 mg/kg/mouse per treat. (4B) Evaluation of therapeutic efficacy. Mouse was implanted with ES-2 cells ($2\times10^5$/mouse) at day 1 and was treated at day 5 and day 10 at indicated dosage. Bioluminescence imaging was captured at day 4 (baseline) and at day 14. Regional delivery of topotecan shows some therapeutic effect. However, regional delivery of Nano-topotecan demonstrated the best therapeutic effect (*, $P<0.05$). (4C) Hazard ratio of overall survival in each group. (4D) White cell count in each group. Experiments were repeated in triplicate.

FIG. 5A-D show exemplary therapeutic effects of regional delivery of Nano-doxorubicin. (A) Treatment schema. Both doxorubicin and Nano-doxorubicin were administered at essential drug 5 mg/kg/mouse per treat. (B) Evaluation of therapeutic efficacy. Mouse was implanted with ES-2 cells ($2\times10^5$/mouse) at day 1 and was treated at day 5 and day 10 at indicated dosage. Bioluminescence imaging was captured at day 4 (baseline) and at day 14. Regional delivery of doxorubicin shows some therapeutic effect. (C) Hazard ratio of overall survival in each group. (D) White cell count in each group. Experiments were repeated in triplicate.

FIG. 6A-D show exemplary therapeutic effects of regional delivery of Abraxane®. (A) Treatment schema. Both Taxol and Abraxane were administered at essential drug 10 mg/kg/mouse per treat. (B) Evaluation of therapeutic efficacy. Mouse was implanted with ES-2 cells ($2\times10^5$/mouse) at day 1 and was treated at day 5, day 8, and day 11 at indicated dosage. Bioluminescence imaging was captured at day 4 (baseline) and at day 14. Regional delivery of Taxol® shows some efficacy. However, regional delivery of Abraxane® demonstrated almost no tumor killing efficacy. EP denotes empty particle (albumin). (C) Hazard ratio of overall survival in each group. (D) White cell count in each group. Experiments were repeated in triplicate.

FIG. 7A-D show illustrative effects of the regional delivery of Nano-Taxol, which suppresses vital organ metastases. (7A) Control of liver metastases. Mouse was induced liver metastases by injection of tumor cells in spleen at d1. Mouse received treatment at d8, d11, and d14 at indicated groups. Liver was retrieved at d18. Regional delivery (intraperitoneal) of Nano-Taxol demonstrated the best control of liver metastases. Representative figures are shown. Arrow indicates tumor. (7B) Control of lung metastases. Mouse was induced lung metastases by tail vein injection of tumor cells at d1. Mouse received treatment at Regional delivery (intrapleural) of Nano-Taxol demonstrated the best control of lung metastases. (7C) Pictures of retroperitoneal lymph node metastases treated with intraperitoneal delivery of Nano-taxol or without (control). (7D) Hazard ratio analysis of overall survival in different organs treated with or without intraperitoneal delivery of Nano-taxol.

FIG. 8A-H show illustrative results of regional delivery of Nano-Taxol exerting more efficient killing of cancer stem cells. (8A) Tumor sphere-forming ability of treated tumor. Mouse was implanted with ES-2 cells ($2\times10^6$/mouse) at day 1 and was treated at day 5, day 8, and day 11 at indicated dosage. Tumors were retrieved at day 14 for each indicated group. Tumors were dissociated into single cell suspension and cultured in an ultralow dish for 10 days. Tumors in the regional delivery of Taxol® shows almost no microsphere formation, while tumors in the other three treated groups (Taxol® i.v., Taxol® i.p., Nano-Taxol i.v.) show increased microsphere formation. Representative figures are shown. (8B) Summary of tumor sphere formation (mean±SD). (8C) Flow cytometry analysis of Hoechst 33342-stained cells and identification of side population cells. Percentage of side population cells are shown. (D-G) RT-PCR analysis for the expressions of stemness marker (8D), genes for epithelial-mesenchymal transition (EMT) driver and expression of epithelial or mesenchymal phenotype (8E), genes for tumor angiogenesis (8F), and genes for multidrug resistance (8G). (8H) CXCR4/CXCL12 axis in stem cells maintenance. Tumors in the regional delivery of Taxol® shows disruption of CXCR4/CXCL12 expression as compared to the control group, while tumors in the other three treated groups (Taxol® i.v., Taxol® i.p., Nano-Taxol i.v.) show increased expression of CXCR4/CXCL12 as compared to the control group. Experiments were repeated in triplicate.

FIG. 11 shows the correlation between BLI and cell growth in vitro. The indicated ES2-luc cell numbers were seeded in 24 wells dish at 37° C. for 24 hrs. BLI were captured after 24 hrs by IVIS-50 system.

FIG. 12A-B shows the correlation between the BLI and the cell growth in SCID mice. The mice were implanted with ES2-luc cells ($5\times10^5$/mouse) on Day 1. BLI were captured on indicated days. One mouse died at Day 17.

FIG. 15A-B show the tumor growth inhibition results of 10 mg/kg Micelle-taxol and 10 mg/kg Nano-taxol treatment. The mice were implanted with ES2-luc cells ($5 \times 10^5$/mouse) on Day 1 and were treated on Day 5, Day 8, and Day 11 with the 10 mg/kg of Nano-taxol or Micelle-taxol. BLI were captured on Day 4 (baseline) and Day 14.

FIG. 16A-G provide the anatomical image of abdominal cavity in tumor bearing mice. Tumor bearing mice showed different degrees of ascites formation. Dissection picture of A (control group) and B (Micelle-taxol i.v. group) showed the most severe ascites with blood. After treatment with Micelle-taxol or Nano-taxol by i.p. (C to G), ascites formation were less than that in A and B. All mice were dissected after the mice died. (A, B on Day 19; C, F, G on Day 21; D, E on Day 26).

FIG. 22A-B shows the correlation between the BLI and the cell growth in SCID mice. The mice were implanted with CT-26-luc cells ($1 \times 10^5$/mouse) on Day 1. Bioluminescence images were captured on indicated days.

DETAILED DESCRIPTION OF THE INVENTION

Figure 1A:
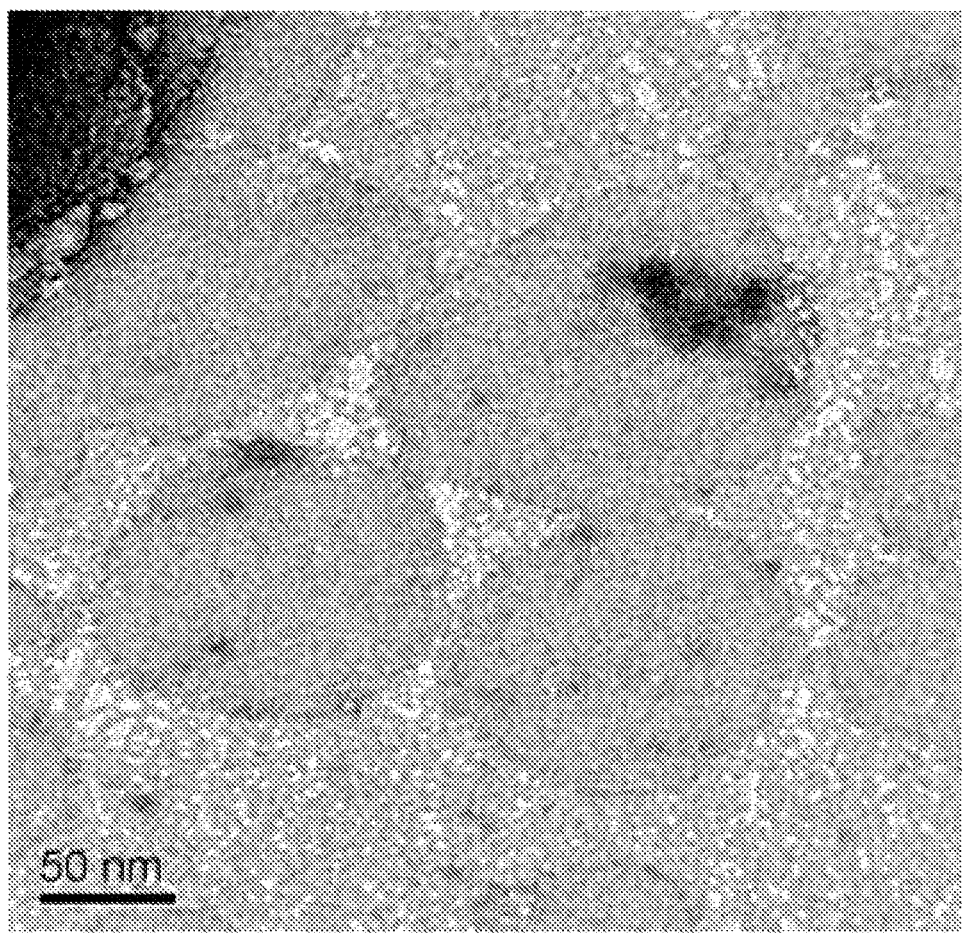
Figure 1B:
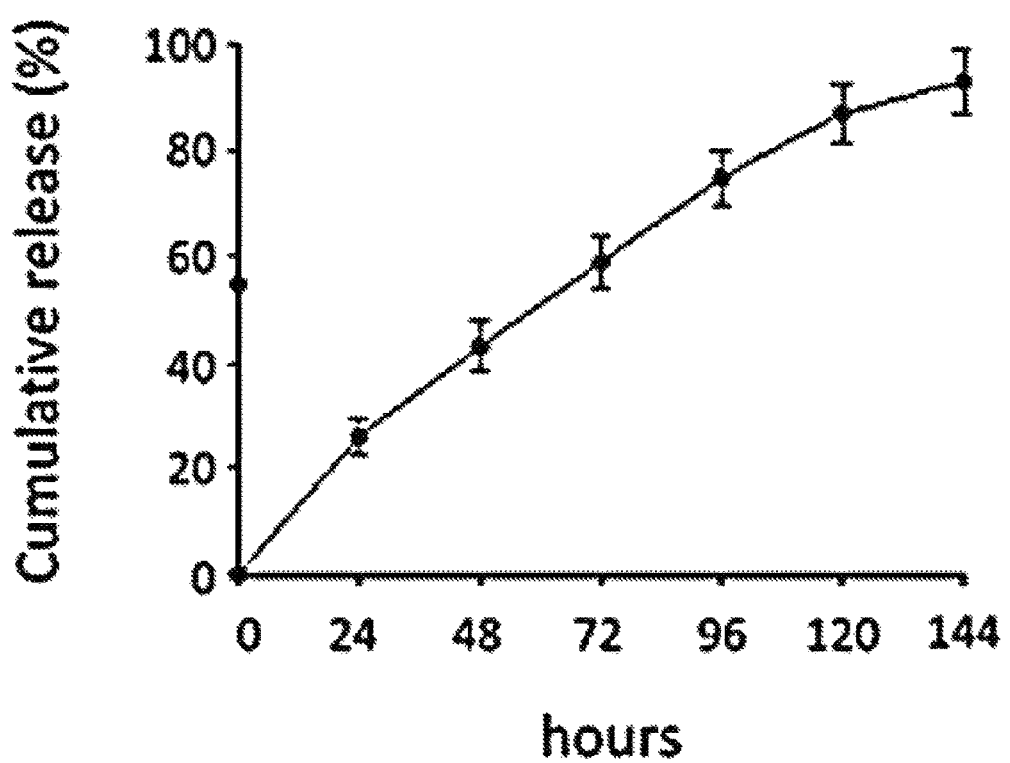
Figure 1C:
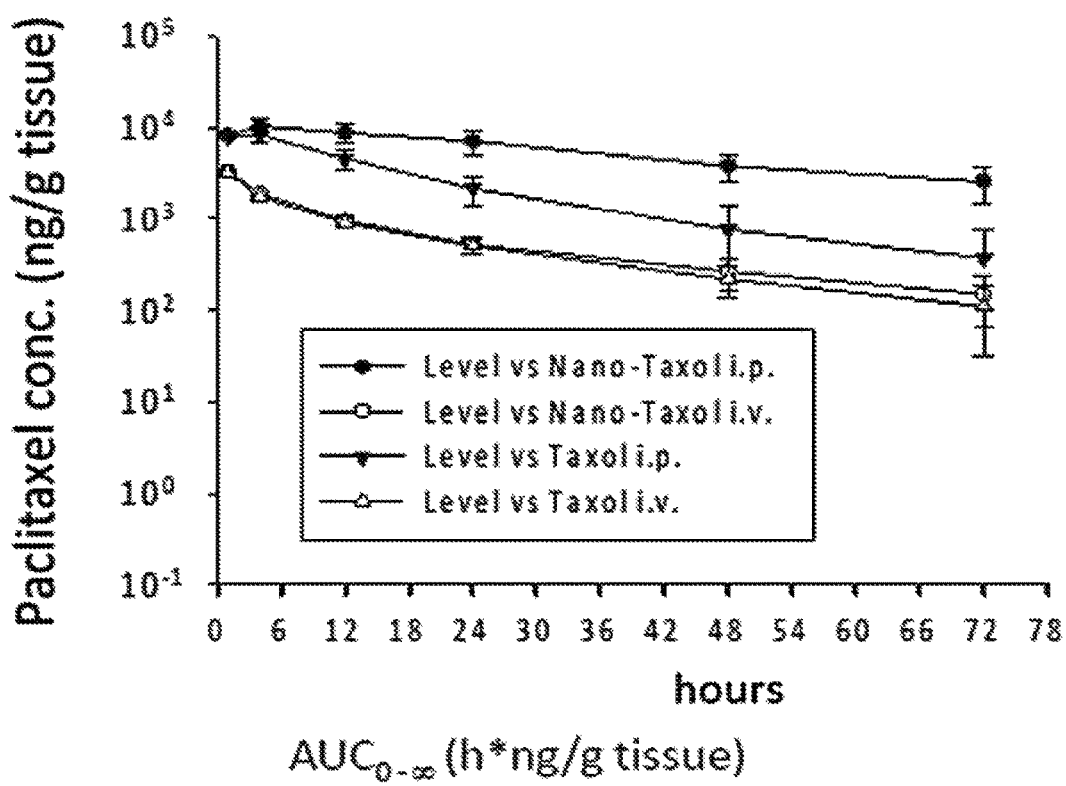

All NPs-based drugs use the EPR effect as a guiding principle. In theory, the use of NPs should take the pharmacokinetic advantage by prolonging the half-life of drugs in the systemic circulation. However, despite this pharmacokinetic advantage and numerous publications and patents of nanotechnology, success is still limited to just a few nanomedicines. Furthermore, one of the major pitfalls in the field of tumor-targeted drug delivery relates to the fact that the EPR effect is often overrated and/or misinterpreted.

Taking examples, although increased tumor accumulation has been confirmed for PEGylated liposomal doxorubicin (DOXIL, Johnson & Johnson Pharmaceutical Research & Development, L.L.C., Raritan, N.J.; CAELYX, Schering-Plough Corporation, Kenilworth, N.J.), the first FDA-approved nanomedicine, the two phase III trials which compared Doxil® to free doxorubicin in the treatment of metastatic breast cancer did not actually translate the EPR effect into statistically significant improvement of tumor response rate and overall survival. Another approved nanomedicine, Abraxane®, an EPR-based albumin-binding paclitaxel, necessitate using 50% higher dose than free paclitaxel to achieve tumor response rate and progression-free survival, still, increase of overall survival was not achieved for metastatic breast cancer (65.o weeks vs. 55.7 weeks, P=0.374). Moreover, the pivotal phase III study leading to the approval of Abraxane® in the treatment of metastatic non-small lung cancer, the median overall survival of Abraxane® was only 12.1 months as compared to 11.2 months of conventional paclitaxel, only 0.9 month survival benefit (P=0.271). Owing to the fact that overall survival remains the gold standard for the evaluation of outcome of a drug, hence, exploiting the EPR effect barely translates into real anti-tumor efficacy for most current approved nanomedicines.

Paclitaxel is a drug used to treat ovarian, breast, lung, pancreatic and other cancers. Paclitaxel was discovered as a result of a U.S. National Cancer Institute-funded screening program; being isolated from the bark of the Pacific yew, *Taxus brevifolia*, thus its name "taxol". Developed commercially by Bristol-Myers Squibb, the generic name has changed to "paclitaxel" with a trademark becoming Taxol. Other trademarks include Abraxane®. Clinicians sometimes use the abbreviation "PTX" for paclitaxel, which is discouraged, because it is not a unique identifier. Thus, unless indicated or described otherwise, paclitaxel is referring to taxol, Taxol, Abraxane®, PTX or other names having the same structure of paclitaxel.

Regional chemotherapy, for example intraperitoneal chemotherapy, takes pharmacokinetic advantage of increased peritoneal-to-plasma area under curve ratio to the tumor-containing peritoneal cavity. Clinically relevant examples of rational uses of regional chemotherapy include the intraperitoneal delivery of cisplatin in patients with ovarian cancer (20-fold increased exposure to the peritoneal cavity as compared to the systemic compartment), and the hepatic artery infusion of floxuridine (15-fold higher tumor drug levels as compared to portal vein infusion of the drug). However, despite this pharmacokinetic advantage, the clinical use of intraperitoneal therapy has been challenged by premature clearance of a small molecular weight drug from the peritoneal cavity, lack of target specificity, and poor drug penetration into the target tissues.

The combination of nanotechnology and regional chemotherapy, i.e. regional delivery of nanomedicine, may compensate for each other's limitations. There are potentially several advantages. First, regional delivery of nanomedicine may take the dual pharmacokinetic advantages, as discussed earlier, of combined regional chemotherapy and NPs. Second, application of hydrophobic, poorly water soluble chemotherapeutic agents for regional delivery carries with some serious problems, since low water solubility results in poor absorption and low bioavailability, nanotechnology can improve the aqueous solubility of poorly soluble drugs and hence may enlist more candidate drugs in the use of regional chemotherapy. Third, the anti-cancer activity of some conventional drugs, such as 5-fluorouracil, gemcitabine, paclitaxel, and camptothecin, is primarily cell cycle-dependent, requiring more prolonged exposure times. The sustained-release function of nanomedicine may solve this inherent limitation. Fourth, rapid clearance usually limits the drug exposure by regional delivery of conventional chemotherapy and creates the need for repeated administration. And further, high drug concentration in the peritoneal cavity of conventional chemotherapy by intraperitoneal delivery usually cause local toxicity. Nanotechnology can potentiate conventional regional chemotherapy by taking advantage of sustained-release capability by which function the aforementioned problems may be solved.

The combination of nanotechnology and conventional chemotherapy has yielded a new therapeutic strategy that is intended to bring critical advances in the fight against cancer. Nanoparticles (NPs), such as liposomes and albumin, currently employed in clinical practice, aim to improve the solubility and efficacy while decreasing the adverse side effects. The enhanced permeability and retention (EPR) effect is becoming the gold standard for the development of nanomedicine.

In order to accelerate the steps of drug development and to investigate whether bypassing the EPR effect may impact the therapeutic efficacy of nanomedicine, in this work, several approved or developing nanomedicines, including liposomal paclitaxel (named as Nano-taxol, Industrial Technology Research Institute, Taiwan), cisplatin-incorporating polymeric micelles (named as Nano-platin, NanoCarrier Co., Ltd., Kashiwa, Japan), polymeric micelle topotecan (named as Nano-topotecan, Taiwan Liposomal Company, Taiwan), PEGylated liposomal doxorubicin (named as Nano-doxorubicin, Doxil,/Caelyx, Merck & Co., Whitehouse Station, N.J., USA), and albumin-bound paclitaxel (named Abraxane®, Celgene, N.J., USA) were tested. A 2-factor factorial design was implemented with factor 1 (systematic delivery versus regional delivery) and factor 2 (free drug versus nanomedicine). For each factorial design, the active drug was given on an equi-dose basis.

In vivo studies of the delivery of selected nanoparticles for treating for example ovarian cancer, colon cancer, or other cancers intraperitoneally were conducted.

In accordance with the practice of the present invention, the drawbacks associated with intraperitoneal chemotherapy of anticancer agents could be overcome by the incorporation of a nano-medicine described herein into special designed delivery matrices, which facilitate sustained drug release. It is provided that the exemplary nano-medicines, such as Nano-taxol and Micelle-taxol, inhibit ovarian tumor growth in vivo following i.p. administration (see e.g., Example 7). Nano-taxol showed dose-dependent antitumor activity and almost completely eradicated ovarian cancer in the peritoneal cavity in 8 out of 11 mice at 20 mg/kg. At 10 mg/kg, tumor eradication was found in 3 of 11 mice and reduced tumor burden in 8 of 11 mice. The response rate was 100%.

Nano-taxol was shown to be effective in the treatment of ovarian cancer by intraperitoneal administration in human xenograft tumor mice model (see e.g., Example 7). To explore the effect of intraperitoneal administration of Nano-taxol in other abdominal cancers, anticancer activity of Nano-taxol by intraperitoneal (i.p.) or intravenous (i.v.) in syngeneic mice model of colon cancer was investigated (see e.g., Example 8). It was found that Nano-taxol inhibited colon cancer CT-26-luc cells growth in vivo following i.p. administration.

In some embodiments provide methods for treating cancer intraperitoneally in a subject comprising administering to said subject in need thereof an anti-cancer agent encapsulated in nanoparticles wherein nanoparticles are characterized to slowly release anti-cancer agent in a timely fashion that allows efficient killing of tumor cells. In certain embodiments, said nanoparticles are characterized to slowly release anti-cancer agent at a rate of 30% or less per 24 hours based on in vitro dissolution study. In some embodiments, the cancer is ovarian cancer, lung cancer, liver cancer, gastric cancer, or colon cancer. In certain embodiments, the cancer is ovarian cancer. In certain embodiments, the cancer is colon cancer.

In certain embodiments, the anti-cancer agents comprise gemcitabine, idarubicin/cytarabine, etopside phosphate, gleevac, temozolomide, bortezomib, letrozole, cetuximab, bevacizumab, paclitaxel, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, lpilimumab, RAD001, Pazopanib, FOLFIRI, BKM120, GSK1120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifarnib/gemcitabline, tootecan, or combinations thereof. In certain embodiments, the anti-cancer agent is paclitaxel.

In some embodiments, said nanoparticles (which an anti-cancer agent encapsulated inside) comprise a first phospholipid which is selected from the group consisting of a hydrogenated naturally-occurring phospholipid and a saturated phospholipid having long carbon chains ($—(CH_2)_n—$, in which n is at least 14), and which has a phase transition temperature $T_{g1}$ ranging between 40 and 74° C.; a second phospholipid which is selected from the group consisting of an unsaturated phospholipid and a saturated phospholipid having short carbon chains ($—(CH_2)_n—$, in which n is at most 14), and which has a phase transition temperature $T_{g2}$ ranging between −30 and 10° C.; liposome-forming materials effective to form a liposome in which the first phospholipid and the second phospholipid coexist in two immiscible phases and create several discontinuous regions, and in which a molar ratio of the first phospholipid to the second phospholipid is at least 3:16; and said anti-cancer agent incorporated in the liposome in an amount of at least 20 mole % to form the formulated liposome. In certain embodiments, the nanoparticles have an incorporation efficiency which remains at least about 70% of incorporation efficiency for six months or more. In certain embodiments, the first phospholipid is selected from the group consisting of phosphatidyl choline (PC), phosphatidyl glycerol (PG), phosphatidyl serine (PS), phosphatidyl acid (PA) and phosphatidyl ethanolamine (PE). In certain embodiments, the first phospholipid is selected from the group consisting of hydrogenated egg phosphatidyl choline (HEPC), hydrogenated soy phosphatidyl choline (HSPC), dipalmitoyl phosphatidyl choline (DPPC) and distearyloyl phosphatidyl choline (DSPC), diarachidoyl phosphatidyl choline, dimyristoyl phosphatidyl ethanolamine (DMPE), dipalmitoyl phosphatidyl ethanolamine (DPPE), distearoyl phosphatidyl ethanolamine (DSPE), dipalmitoyl phosphatidyl glycerol (DPPG), distearoyl phosphatidyl glycerol, dimyristoyl phosphatidyl acid (DMPA), dipalmitoyl phosphatidyl acid (DPPA), dipalmitoyl phosphatidyl serine (DPPS), and distearoyl phosphatidyl serine (DSPS). A non exclusive exemplary nanoparticle described herein is Nano-taxol.

In some embodiments, the nanoparticles suitable for treating cancer intraperitoneally disclosed herein comprise one or more block copolymers comprising a hydrophobic block, a hydrophilic block bonded to the hydrophobic block, and one or more zwitterions. In certain embodiments, the zwitterion having one positive charge and one negative charge, is bonded to a terminal end of the hydrophobic block. In certain embodiments, the hydrophobic block is polycaprolactone (PCL), polyvalerolactone (PVL), poly(lactide-co-glycolide) (PLGA), polylactic acid (PLA), polybutyrolactone (PBL), polyglycolide, or polypropiolactone (PPL); and the hydrophilic block is polyethylene glycol (PEG), hyaluronic acid (HA) or poly-γ-glutamic acid (PGA).

In some embodiments, the nanoparticles suitable for treating cancer intraperitoneally disclosed herein comprise a polymeric micelle (such as Micelle-taxol) comprising a block copolymer of the following formula:

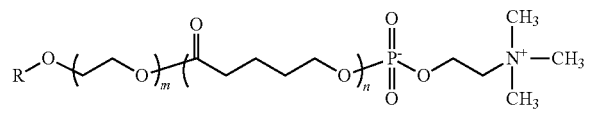

wherein R represents a hydrogen atom, a $C_{1-6}$ alkyl group, a benzyl group or an acyl group; and m and n, are each independently an integer of 10-100. In certain embodiments, the polymeric micelle has a diameter ranging from about 20 nm to about 1,000 nm. In certain embodiments, the polymeric micelle has a hydrophobic interior and a hydrophilic surface.

In some embodiments provide methods for treating cancer via regional delivery in a subject comprising administering to said subject in need thereof an anti-cancer agent encapsulated in sustained release nanoparticles wherein the anti-cancer agent nanoparticles are administered intrapleurally. In certain embodiments, the cancer is ovarian cancer, lung cancer, liver cancer, gastric cancer, or colon cancer. In certain embodiments, said cancer is metastasis. In some embodiments, said subject has severe adhesion in the peritoneal cavity. In certain embodiments, said anti-cancer agent is paclitaxel.

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. an anti-cancer agent encapsulated in nanoparticles described herein and a co-agent, are both administered to a patient simultaneously in the form of a single entity or dosage. The term "non-fixed combination" means that the active ingredients, e.g. an anti-cancer agent encapsulated in nanoparticles described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of an anti-cancer agent encapsulated in nanoparticles described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Formulation

In some embodiments provide pharmaceutical compositions comprising a therapeutically effective amount of paclitaxel nanoparticles prepared in accordance with the practice of U.S. Pat. No. 7,485,320, U.S. Pat. No. 8,124,128, and U.S. Pat. No. 8,420,119 (each of which are incorporated herein by reference for such disclosure).

In some embodiments, invention nanoparticles comprise an anti-cancer agent (e.g., paclitaxel) encapsulated inside the nanoparticles comprising a first phospholipid which is selected from the group consisting of a hydrogenated naturally-occurring phospholipid and a saturated phospholipid having long carbon chains (—$(CH2)_n$—, in which n is at least 14), and which has a phase transition temperature $T_{g1}$ ranging between 40 and 74° C.; a second phospholipid which is selected from the group consisting of an unsaturated phospholipid and a saturated phospholipid having short carbon chains (—$(CH2)_n$—, in which n is at most 14), and which has a phase transition temperature $T_{g2}$ ranging between −30 and 10° C.; liposome-forming materials effective to form a liposome in which the first phospholipid and the second phospholipid coexist in two immiscible phases and create several discontinuous regions, and in which a molar ratio of the first phospholipid to the second phospholipid is at least 3:16; and said anti-cancer agent incorporated in the liposome in an amount of at least 20 mole % to form the formulated liposome. In certain embodiments, the formulated nanoparticles has an incorporation efficiency which remains at least about 70% of incorporation efficiency for six months or more. In certain embodiments, the first phospholipid is selected from the group consisting of phosphatidyl choline (PC), phosphatidyl glycerol (PG), phosphatidyl serine (PS), phosphatidyl acid (PA) and phosphatidyl ethanolamine (PE). In certain embodiments, the first phospholipid is selected from the group consisting of hydrogenated egg phosphatidyl choline (HEPC), hydrogenated soy phosphatidyl choline (HSPC), dipalmitoyl phosphatidyl choline (DPPC) and distearyloyl phosphatidyl choline (DSPC), diarachidoyl phosphatidyl choline, dimyristoyl phosphatidyl ethanolamine (DMPE), dipalmitoyl phosphatidyl ethanolamine (DPPE), distearoyl phosphatidyl ethanolamine (DSPE), dipalmitoyl phosphatidyl glycerol (DPPG), distearoyl phosphatidyl glycerol, dimyristoyl phosphatidyl acid (DMPA), dipalmitoyl phosphatidyl acid (DPPA), dipalmitoyl phosphatidyl serine (DPPS), and distearoyl phosphatidyl serine (DSPS). A non exclusive exemplary nanoparticle described herein is Nano-taxol.

In some embodiments, invention nanoparticles comprise an anti-cancer agent (such as paclitaxel) encapsulated inside the nanoparticles comprising one or more block copolymer which comprises: a hydrophobic block, a hydrophilic block bonded to the hydrophobic block, and only one zwitterion, wherein the zwitterion, having one positive charge and one negative charge, is bonded to a terminal end of the hydrophobic block; the hydrophobic block is polycaprolactone (PCL), polyvalerolactone (PVL), poly(lactide-co-glycolide) (PLGA), polylactic acid (PLA), polybutyrolactone (PBL), polyglycolide, or polypropiolactone (PPL); and the hydrophilic block is polyethylene glycol (PEG), hyaluronic acid (HA) or poly-γ-glutamic acid (PGA).

In some embodiments, invention nanoparticles comprise an anti-cancer agent (e.g., paclitaxel) encapsulated within a polymeric micelle such as Micelle-taxol, which comprises a block copolymer of the following formula:

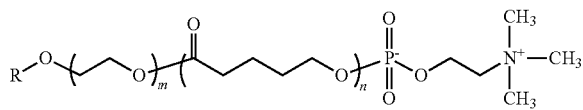

wherein R represents a hydrogen atom, a $C_{1-6}$ alkyl group, a benzyl group or an acyl group; and m and n, which may be the same or different, are each an integer of 10-100.

The anti-cancer agents for example may be gemcitabine, idarubicin/cytarabine, etopside phosphate, gleevac, temozolomide, bortezomib, letrozole, cetuximab, bevacizumab, paclitaxel, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, lpilimumab, RAD001, Pazopanib, FOLFIRI, BKM120, GSK1120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifarnib/gemcitabline, tootecan, or combinations thereof. A skilled person in the art would readily choose other anti-cancer agent suitable in accordance with the practice of this invention. In certain embodiments, the anti-cancer agent is paclitaxel.

Figure 10:
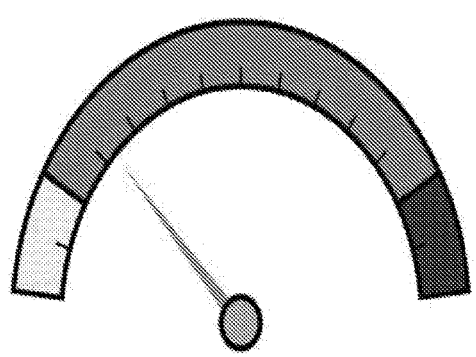
FIG. 10 provides guidance to prepare proper nanoparticles in accordance with the practice of the present invention. At the two extremes (Too loose or too tight conjugates), nanomedicine produce unsatisfactory tumor killing. Too loose conjugates behave like free drug which produces moderate effect. Too tight conjugates produce almost no effect. Only regional delivery of sustained-release nanomedicine in a timely fashion produces satisfactory tumor killing.

In some embodiments, invention nanoparticles comprise any anti-cancer agents encapsulated in suitable nanoparticles (e.g., Nano-taxol) or polymeric micelles (e.g., Micelle-taxol) where said anticancer agent is sustained-released in a timely fashion that allow efficient killing of tumor cells based on FIG. 10.

In some embodiments, invention paclitaxel nanoparticle comprise paclitaxel encapsulated in any suitable nanoparticles (e.g., Nano-taxol) or polymeric micelles (e.g., Micelle-taxol) where paclitaxel is sustained-released in a timely fashion that allows efficient killing of tumor cells based on FIG. 10.

In some embodiments, nanoparticles are characterized to slowly release anti-cancer agent at a rate of 30% or less per 8 hours based on dialysis. See examples (e.g., FIG. 1 and Table 2) from U.S. Pat. No. 8,420,119.

In some embodiments provide pharmaceutical compositions, as used herein, refers to a mixture of invention nanoparticles with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of nanoparticles described herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the anticancer used and other factors. The nanoparticles described herein are used singly or in combination with one or more therapeutic agents as components of mixtures.

Methods for the preparation of compositions comprising invention nanoparticles described herein include formulating the nanoparticles with one or more inert, pharmaceutically acceptable excipients or carriers to form a solid, semi-solid or liquid. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

Pharmaceutical compositions also, optionally include solubilizing agents to aid in the solubility of invention nanoparticles. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions in some embodiments optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Exemplary suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

General Consideration for Combination Treatments

In general, the compositions described herein and, in embodiments where combinational therapy is employed based on the mode of action described herein, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

EXAMPLES

Example 1. Preparation of Animal Models and Cell Lines for Tumor Generation

A single intraperitoneal injection of human ovarian cancer cell line ES-2 ($2\times10^5$ cells per mouse, ATCC no. CRL-1978) at d0 into 5-week-old SCID mice (CB.17 scid/scid) was commenced to generate tumor, which was confirmed via abdominal distension and malignant ascites in 3 weeks. Animals were purchased from the National Laboratory Animal Breeding and Research Center, Taipei, and kept in the oncology animal facility of the Taipei Veterans Hospital (Taipei, Taiwan). Animals were used in compliance with institutional animal health care regulations, and all animal experimental procedures were approved by the Institutional Animal Care and Use Committee. Tumor-bearing mice were euthanized at the endpoint when there were signs of distress, including fur ruffling, rapid respiratory rate, hunched posture, reduced activity, and progressive ascites formation. Groups of mice were treated. A 2-factor factorial design was implemented with factor 1 (systematic delivery versus regional delivery) and factor 2 (free drug versus nanomedicine). For each factorial design, the active drug was given on an equi-dose basis. Several approved or developing nanomedicines, including exemplary paclitaxel nanoparticle (e.g., liposomal paclitaxel, named as Nano-taxol, Industrial Technology Research Institute, Taiwan), cisplatin-incorporating polymeric micelles (named as Nano-platin, NanoCarrier Co., Ltd., Kashiwa, Japan), polymeric micelle topotecan (named as Nano-topotecan, Taiwan Liposomal Company, Taiwan), pegylated liposomal doxorubicin (named as Nano-doxorubicin, Doxil,/Caelyx, Merck & Co., Whitehouse Station, N.J., USA), and albumin-bound paclitaxel (named Abraxane®, Celgene, N.J., USA). The dosing schedule for each paired drugs (free drug and nanomedicine) was given on maximal tolerated dose based on preliminary study. Lung metastases were induced by tail-vein injection, while liver metastases were by splenic injection, and retroperitoneal lymphatic metastases were induced by intra-uterine injection of tumor cells. The compositions of each nanomedicines can be found from and are based on the sources of each nanomedicine. For example, Nano-taxol received comprises hydrogenated soy phosphatidylcholine (HSPC), cholesterol, d-alpha-tocopheryl polyethylene glycol succinate.

Example 2. Paclitaxel Assay in Tumor Tissue

In Vitro Release Kinetics of Paclitaxel Nanoparticles by HPLC

Assay of release of exemplary paclitaxel nanoparticles (e.g., paclitaxel from liposomes) was performed using the dialysis method at room temperature, and was compared with that from paclitaxel without any nanoparticle treatment ("free paclitaxel"). After reconstituting the freeze-dried liposomes in PBS (pH 7.4) to make 1.5 mg/mL of paclitaxel, an aliquot of each liposomal dispersion (0.1 mL) was placed in a dialysis tube (MWCO 6000-8000, Gene Bio-Application Ltd., Israel) and was tightly sealed. Afterward, the tube was immersed in 200 mL of release medium, i.e., PBS (pH 7.4) containing 0.1% (v/v) Tween 80 to maintain sink condition. While stirring the release medium using the magnetic stirrer at 300 rpm, samples (0.5 mL) were taken at predetermined time intervals from the release medium for 24 h, which was refilled with the same volume of fresh medium. Concentration of paclitaxel was determined by HPLC after appropriate dilution with acetonitrile without further treatment.

Analyses of paclitaxel concentration were performed on an Agilent 1100 series chromatographic system (Agilent Technologies, Palo Alto, Calif., USA). Chromatographic separation was achieved with a $C_{18}$Altima™ column (4.6 mm ID, 150 mm; 5 µm) from Grace (Grace, Mass.) protected by a Phenomenex® SecurityGuard™ in-line filter frit (Torrance, Calif., USA). The mobile phase consisted of water, methanol, and acetonitrile (25:35:40, v/v). The mobile phase was filtered through a 0.45-µm filter (Millipore, Bedford, Mass., USA) and degassed before analysis. The high-performance liquid chromatography (HPLC) system was run at ambient temperature with a flow-rate of 1.0 mL/min, and quantitative analysis of peak area under the curve was performed at a wavelength of 230 nm with total chromatographic run time of 8 min. The calibration curve for the quantification of paclitaxel was linear over the standard concentration range of paclitaxel at 50-50,000 ng/mL with a correlation coefficient of $R^2=0.999$. The limit of detection was 50 ng/mL.

In this experiment, Nano-taxol is used as the major test drug to harbor sustained-release function. Transmission electron microscopy of this drug is presented (see FIG. 1A). Applying kinetic equation models, the release process was calculated by treating release profile mathematically using zero-order, first-order and Higuchi equations (T. Higuchi, Rate of release of medicaments from ointment bases containing drugs in suspension, Journal of pharmaceutical sciences, 50 (1961) 874-875). Higher correlation coefficients were obtained for the Higuchi equation, indicating the release of the free drug based on in vitro drug dissolution study was found to be sustained-released and was driven mainly by a diffusion-controlled mechanism at the rate of 30% or less per 24 hours, as the plots showed high linearity, with correlation coefficient ($R^2$) value of 0.9864 (FIG. 1B), as seen in other known liposomal products. Increased area under the curve of intra-tumor drug concentration (FIG. 1C) and apoptosis (FIG. 1D) were observed in the group of regional delivery of Nano-taxol.

Example 3: Determining Synergism of Regional Delivery of Nanomedicine by Chou-Talalay Method There were six dose levels used to evaluate the synergy effect. To calculate combined drug effects, the combination index (CI)-isobologram method of Chou-Talalay was used. Regional delivery of exemplary paclitaxel nanoparticle (e.g., Nano-taxol) was viewed to determine the combined effect, while systematic delivery of Nano-taxol or regional delivery of free paclitaxel (Taxol®) was viewed as a single effect. Chou-Talalay method involves plotting of dose-effect curves for each agent and combinations thereof in multiply diluted concentrations by using the median-effect equation, calculating how much the experimental effect differs from the effect expected with additive effects. CI=1, <1, and >1 indicate additive effect, synergism, and antagonism, respectively. The CI values can be determined at different effect and different dose levels, and the isobolograms can be automatically generated by using Compusyn software.

Figure 1E:
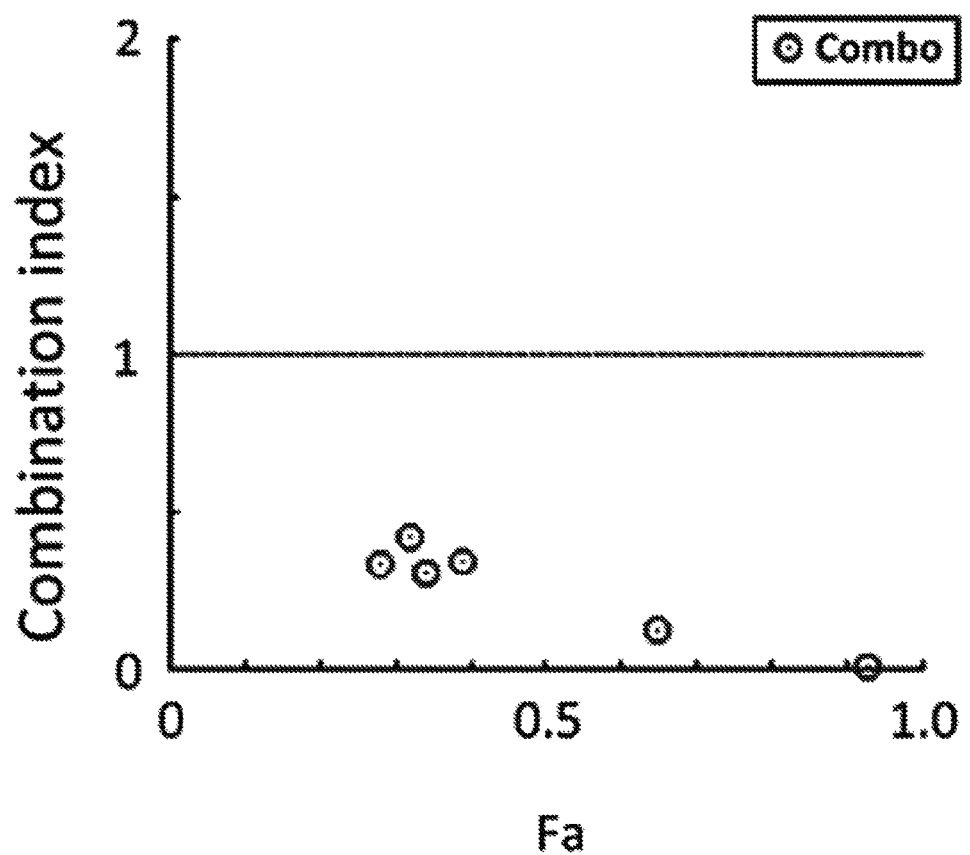
Figure 1F:
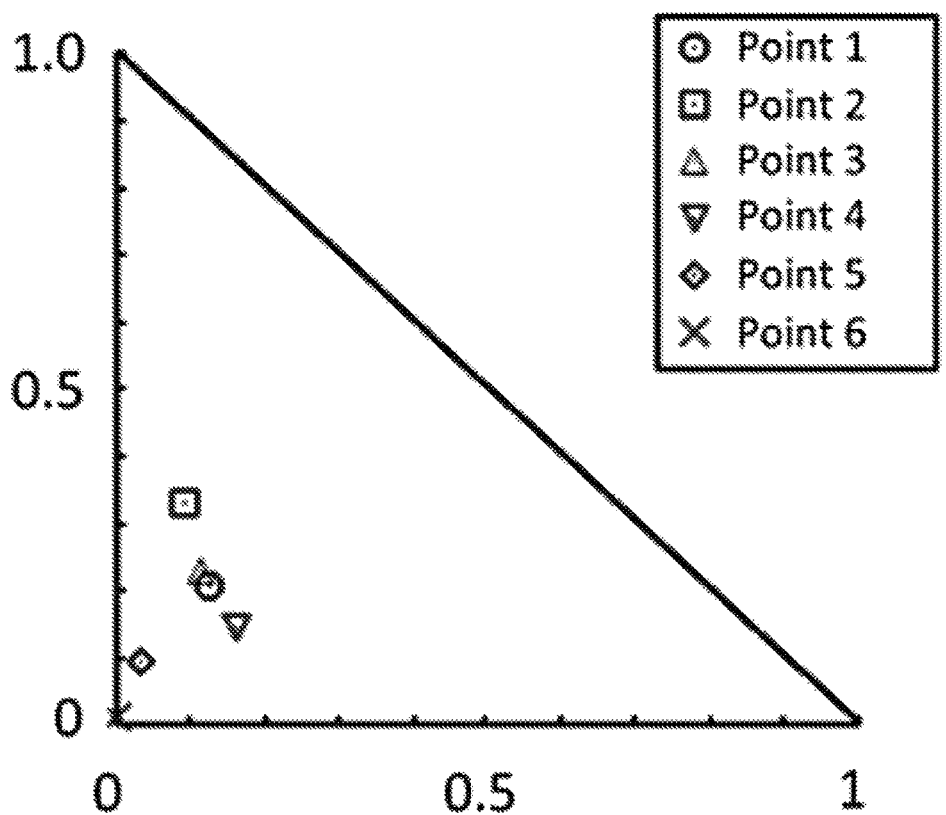

The Fa-CI plot demonstrating drug combination index are all less than 1, indicating that regional delivery of Nano-taxol produces synergistic tumor killing than either drug alone (systematic delivery of Nano-taxol or regional delivery of free Taxol®)(FIG. 1E). Furthermore, normalized isobologram for combinations at different combination ratios also demonstrates synergistic tumor killing effect (FIG. 1F).

Figure 2A:
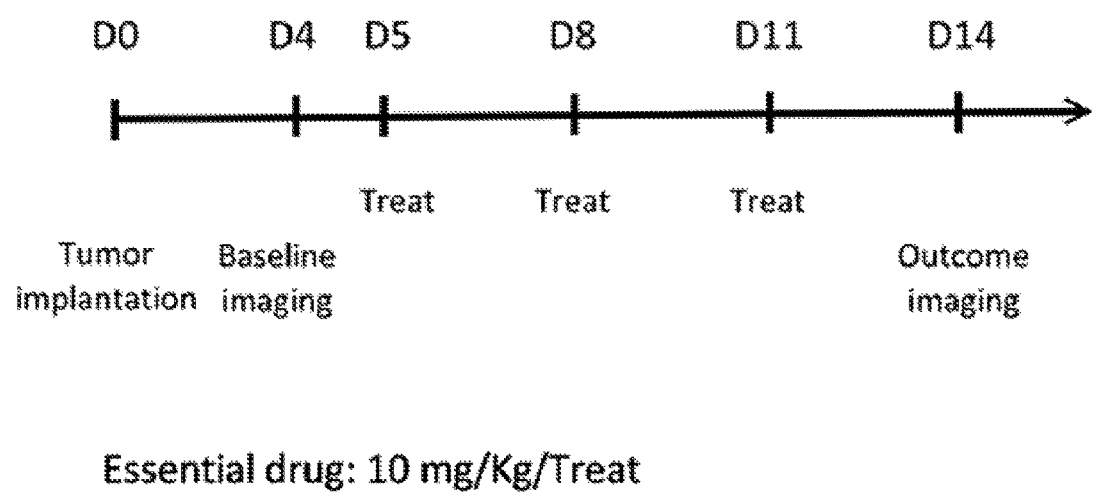
FIG. 2A-D show exemplary therapeutic effects of regional delivery of Nano-Taxol. (2A) Treatment schema. Both Taxol and Nano-Taxol were administered at essential drug 10 mg/kg/mouse per treat. (2B) Evaluation of therapeutic efficacy. Mouse was implanted with ES-2 cells ($2\times10^5$/mouse) at day 1 and was treated at day 5, day 8, and day 11 at indicated dosage. Bioluminescence imaging was captured at day 4 (baseline) and at day 14. Regional delivery of Taxol® shows some efficacy. However, regional delivery of Nano-Taxol® demonstrated the best tumor killing efficacy. Cremophor EL is a vehicle for paclitaxel. EP, empty particles. (2C) Hazard ratio of overall survival in each group. Regional delivery of Nano-Taxol shows a hazard ratio of only 0.4 (*, P<0.05). (2D) White cell count in each group. The mean white cell count in the regional delivery of Nano-Taxol group is not statistically different from the systematic delivery of Taxol® group. Experiments were repeated in triplicate.
Figure 2B:
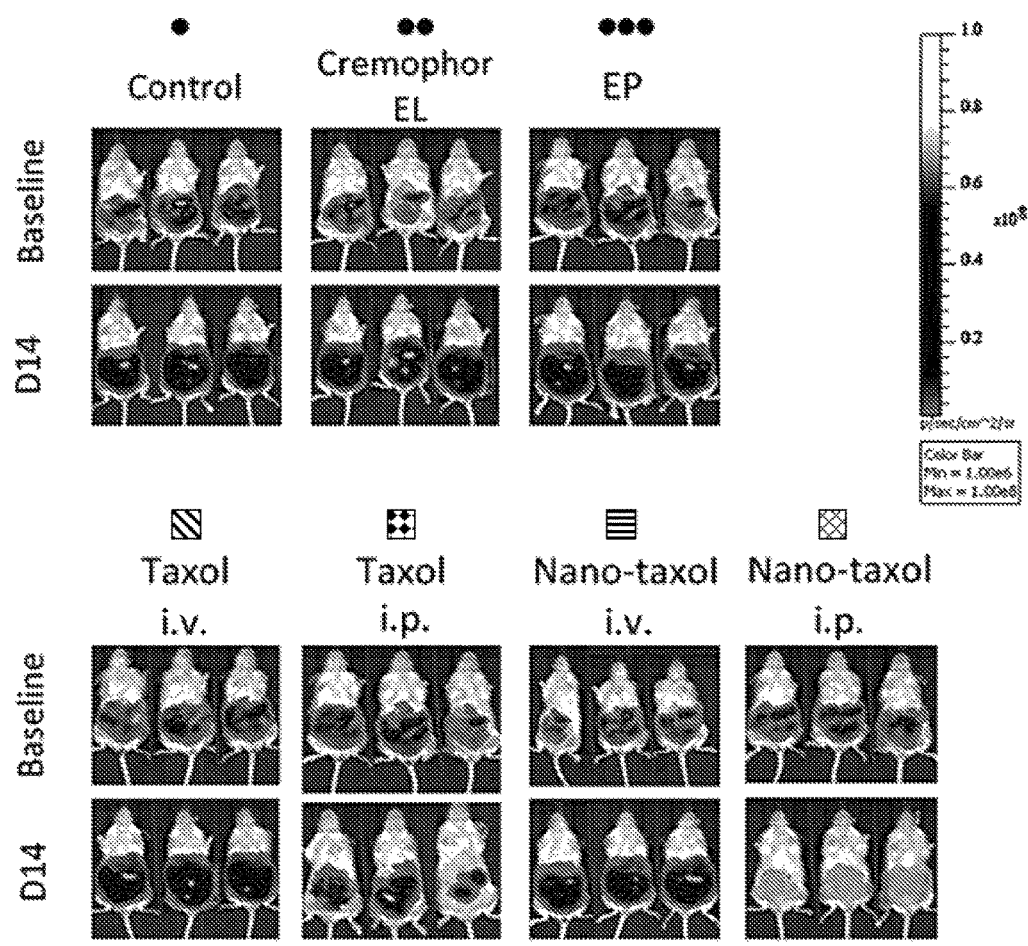
Figure 3A:
Figure 3C:
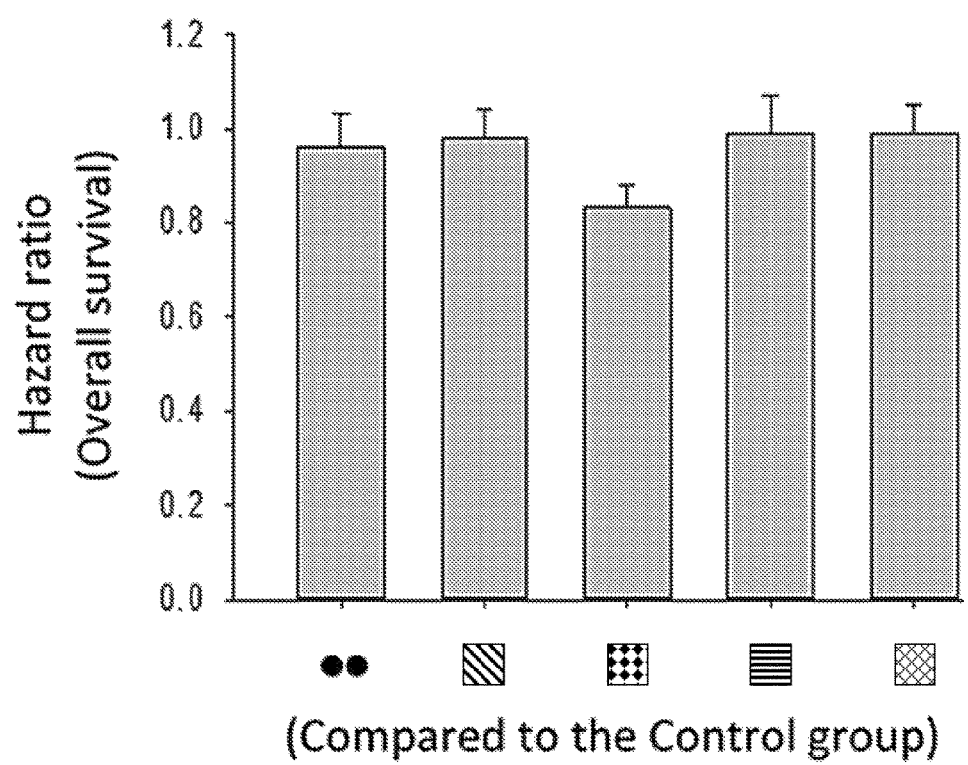
Figure 3D:
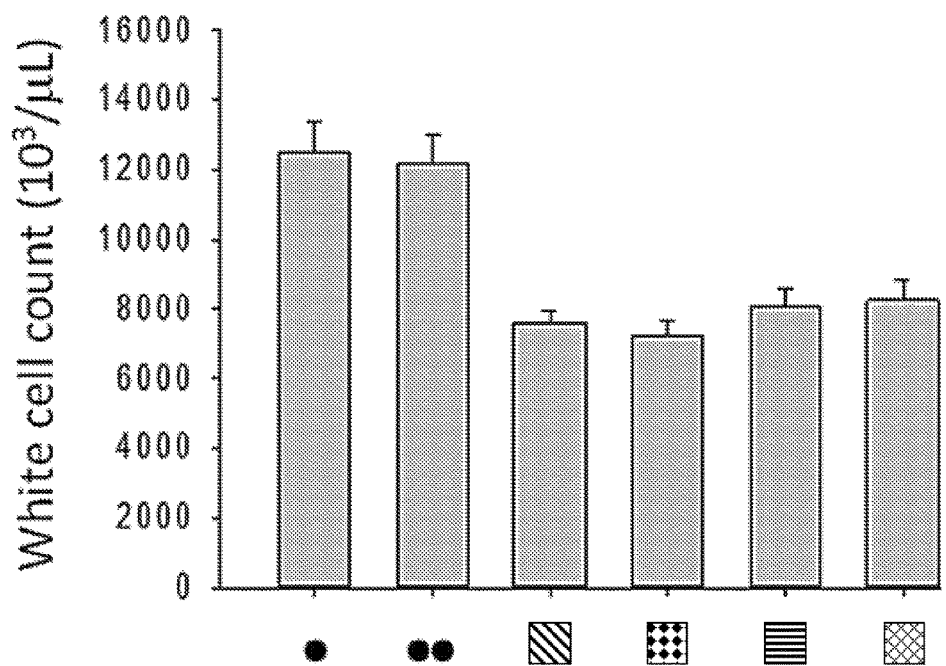
Figure 4B:
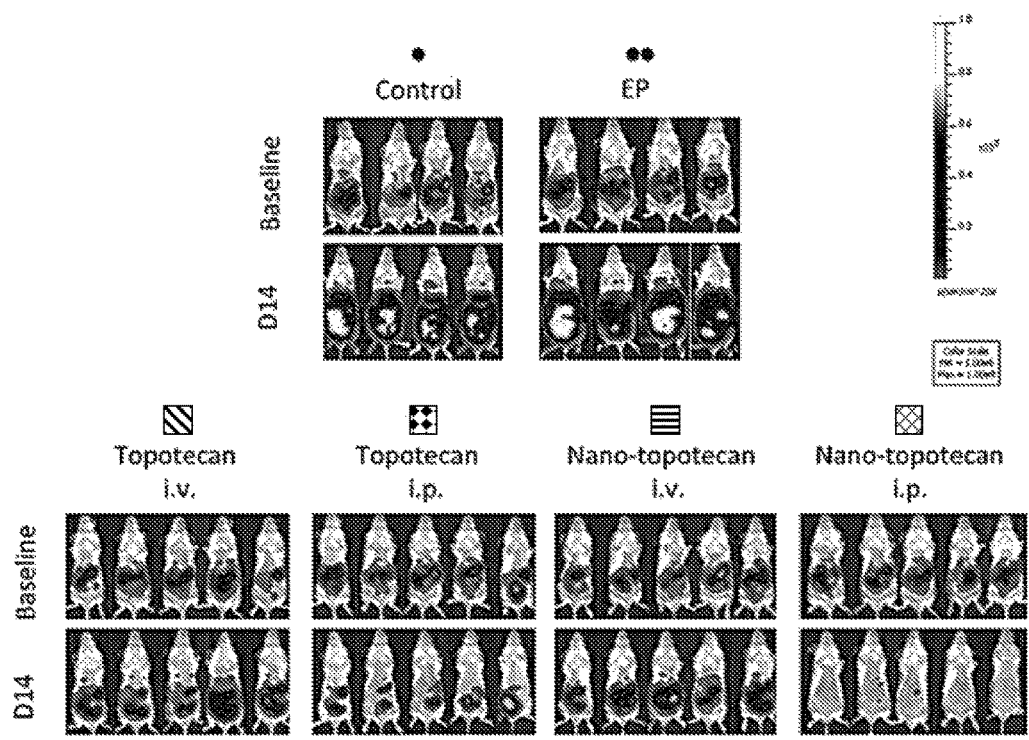
Figure 4C:
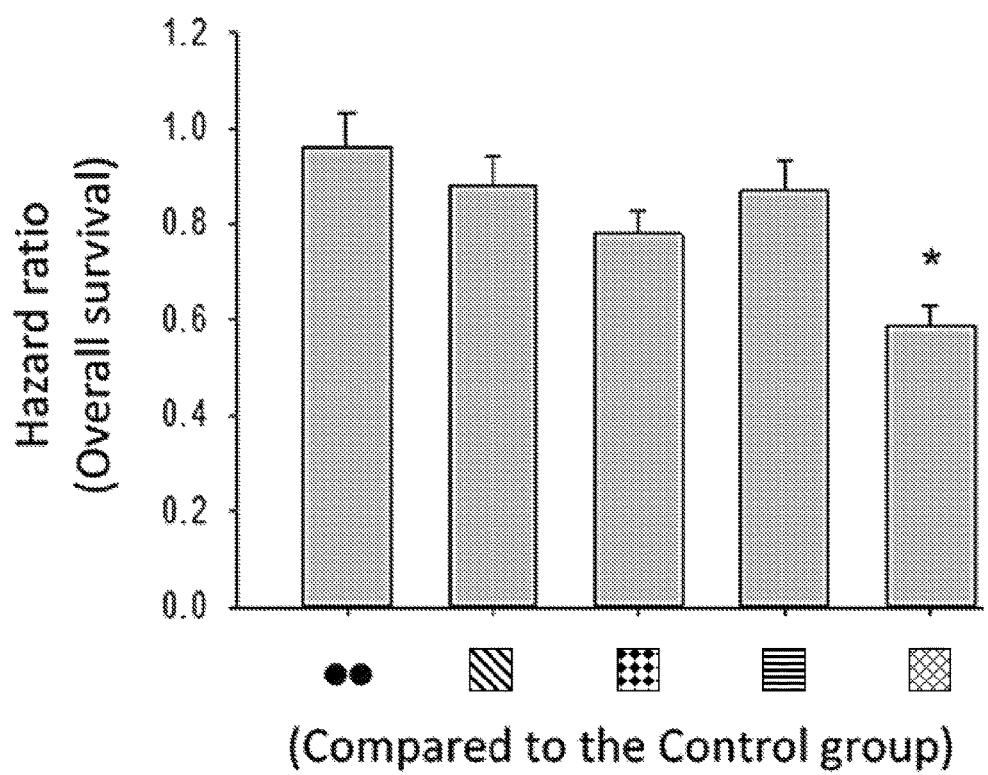
Figure 4D:
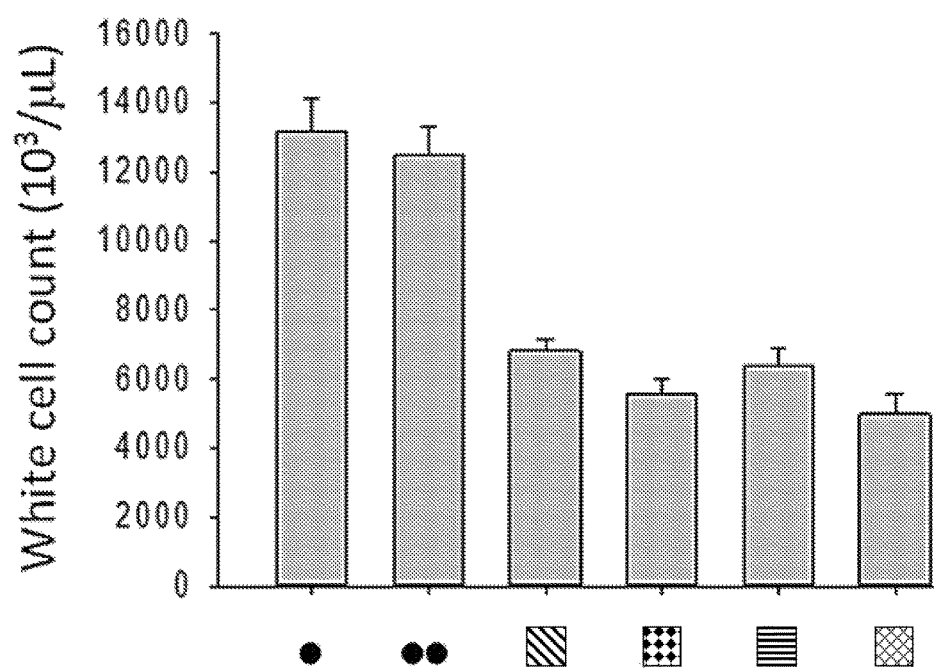
Figure 5B:
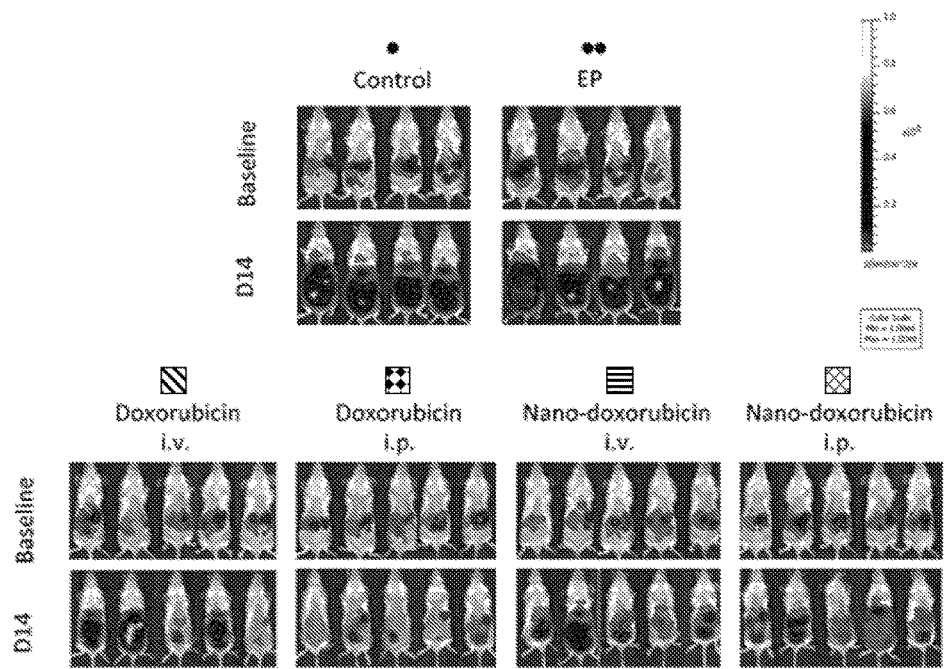
Figure 5C:
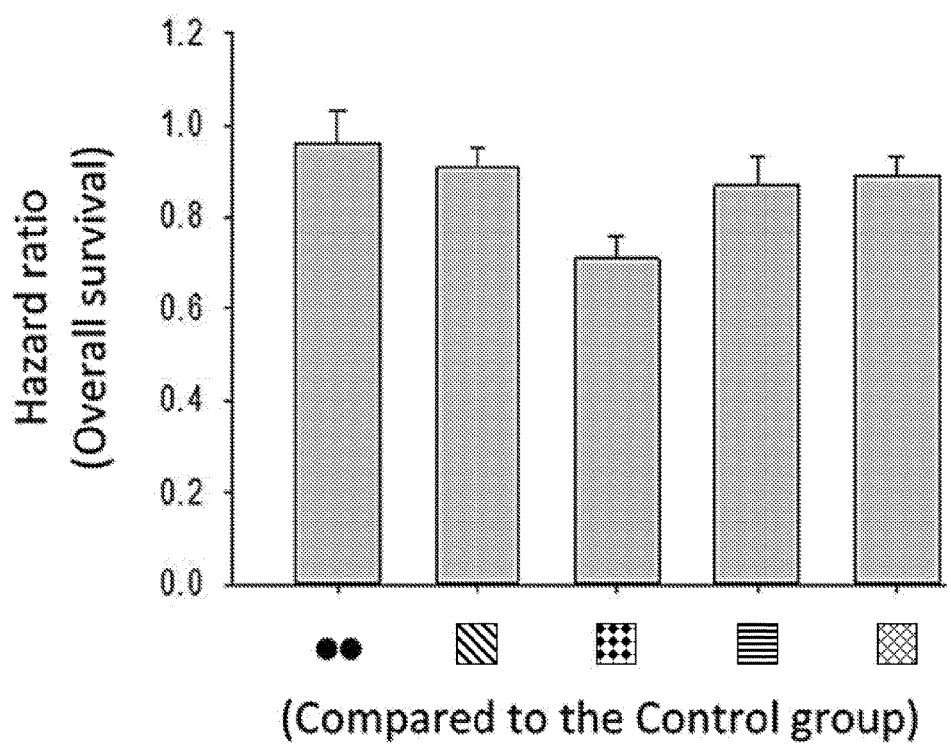

Next whether the synergy tumor killing effect could be translated into real tumor killing was examined. Under the treatment schema (FIG. 2A), regional delivery of sustained-released Nano-taxol performs the best tumor killing than any treatment modality (FIG. 2B). Regional delivery of Nano-topotecan also showed the same therapeutic effects (FIG. 4). However, regional delivery of Nano-platin (FIG. 3), Nano-doxorubicin (FIG. 5) and Abraxane® (FIG. 6) did not show such therapeutic benefit. Notably, intraperitoneal delivery of Taxol® (FIG. 2B), cisplatin (FIG. 3), topotecan (FIG. 4), and doxorubicin (FIG. 5) do show some therapeutic benefit in the current study, which paralleled the results in each corresponding human trials (see e.g., D. S. Alberts, P. Y. Liu, E. V. Hannigan, R. O'Toole, S. D. Williams, J. A. Young, E. W. Franklin, D. L. Clarke-Pearson, V. K. Malviya, B. DuBeshter, Intraperitoneal cisplatin plus intravenous cyclophosphamide versus intravenous cisplatin plus intravenous cyclophosphamide for stage III ovarian cancer, The New England journal of medicine, 335 (1996) 1950-1955.-28; D. K. Armstrong, B. Bundy, L. Wenzel, H. Q. Huang, R. Baergen, S. Lele, L. J. Copeland, J. L. Walker, R. A. Burger, G. Gynecologic Oncology, Intraperitoneal cisplatin and paclitaxel in ovarian cancer, The New England journal of medicine, 354 (2006) 34-43; H. G. Muntz, T. W. Malpass, K. F. McGonigle, M. D. Robertson, P. L. Weiden, Phase 2 study of intraperitoneal topotecan as consolidation chemotherapy in ovarian and primary peritoneal carcinoma, Cancer, 113 (2008) 490-496; G. Delgado, R. K. Potkul, J. A. Treat, G. S. Lewandowski, J. F. Barter, D. Forst, A. Rahman, A phase I/II study of intraperitoneally administered doxorubicin entrapped in cardiolipin liposomes in patients with ovarian cancer, American journal of obstetrics and gynecology, 160 (1989) 812-817; discussion 817-819).

Viewed in depth, the present invention demonstrates that systematic delivery of nanomedicines (e.g., exploiting the EPR effect) did not show therapeutic benefit compared to each corresponding free drug, implicating that the exploiting the EPR effect barely translate into real therapeutic effect. Furthermore, while regional delivery of all free drugs showed some therapeutic effects, not all regional delivery of nanomedicines showed therapeutic effects (yes to Nano-taxol and Nano-topotecan, but no to Nano-doxorubicin and Abraxane®), showing that free drug of Nano-doxorubicin and Abraxane® forms too stable conjugates with NPs and do not release free drug in a timely manner to control intraperitoneal tumors. Hence, not all nanomedicines are suitable for regional therapy.

Figure 2C:
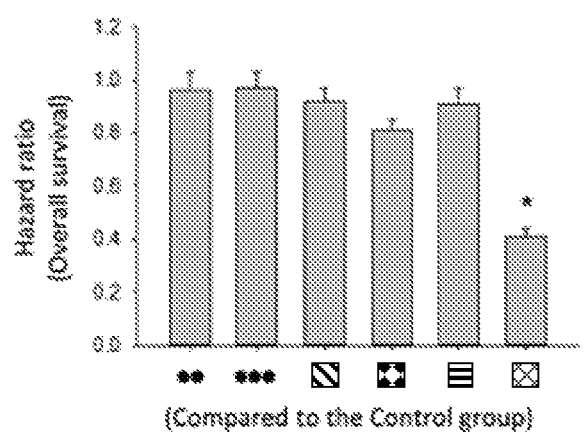
Figure 2D:
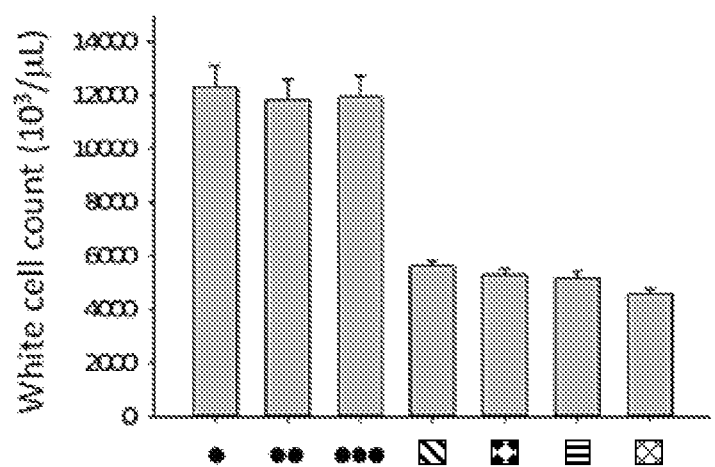

Hazard ratio of overall survival demonstrates that regional delivery of Nano-taxol confers the longest survival (FIG. 2C). Decrease of white cell count is not statistically different between each treated group (FIG. 2D).

In some embodiments, there are provided methods of regional delivery of sustained-release nanomedicine where said nanomedicine suppresses vital organ metastases.

Figure 7A:
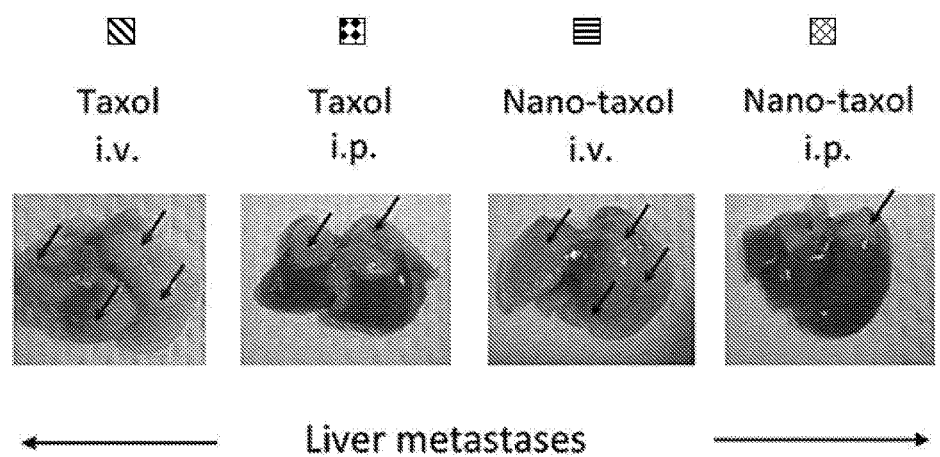

Although direct intraperitoneal dissemination is very common, ovarian cancer may also metastasize through the lymphatic channels and the hematogenous route. The effects of consequent vital organ metastases (e.g., liver or lung) are devastating with dismal prognosis despite current standard treatment of systematic delivery of Taxol®. Compared to systemic delivery of Taxol®, intraperitoneal delivery of Nano-taxol significantly suppressed tumor metastases to liver (FIG. 7A).

Figure 7B:
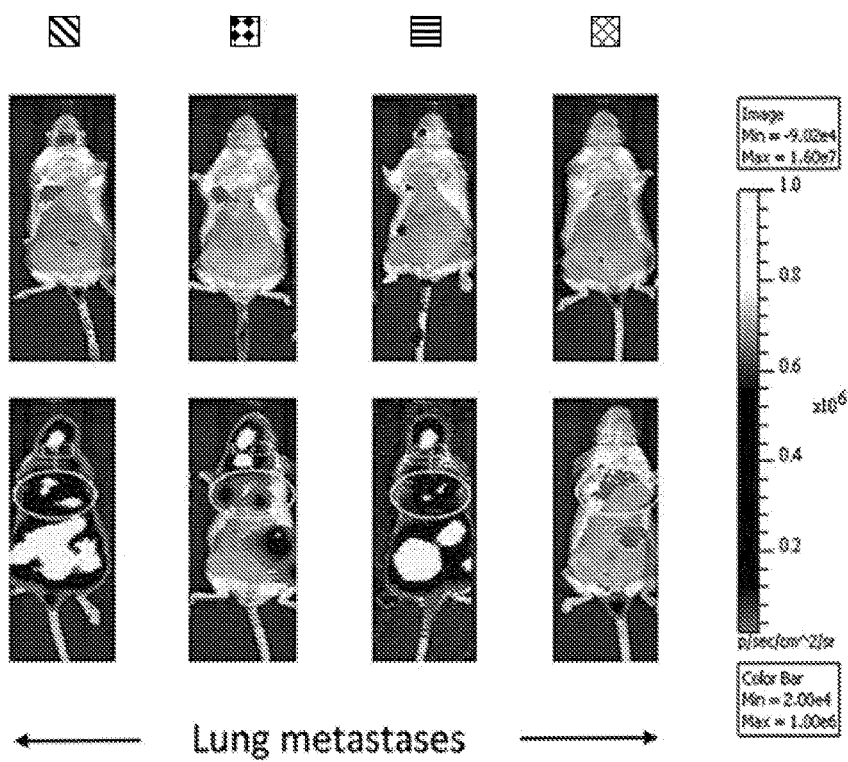

Owing to the findings of evident ovarian cancer tumor killing by regional delivery of Nano-taxol, in accordance with the practice of the present invention, the application of regional delivery of invention nanoparticle is applied in the treatment of other cancer such as lung metastases. For example, the animal study of lung metastases (mouse model) shows that intrapleural delivery of Nano-taxol produced the best control of lung metastases (FIG. 7B). In contrast, the current standard therapy of systematic delivery of Taxol® showed unsatisfactory control of tumor. Although intrapleural deliver of Taxol® shows some therapeutic efficacy, regional delivery of Nano-taxol in accordance with the practice of the present invention outperforms regional delivery of Taxol®. Currently, metastases of ovarian cancer to lung carry poor prognosis despite standard systematic therapy. Intrapleural delivery of Nano-Taxol demonstrates satisfactory suppression of lung metastases, and even suppression of intraperitoneal metastases.

Without being bound by any theories, based on the finding described herein, regional delivery of nanomedicine could be viewed as delivery of nanomedicine into a reservoir. Once a reservoir is failed, for example, due to severe adhesion induced by carcinomatosis in the peritoneal cavity (the largest cavity in the human), in accordance with the practice of the present invention, the pleural cavity can replace the peritoneal cavity as a reservoir for delivery of nanomedicine. The sustained-release of free drug from a reservoir effectively controls local tumor (e.g., lung metastases) but also distant metastases (e.g., intraperitoneal metastases).

Figure 7D:
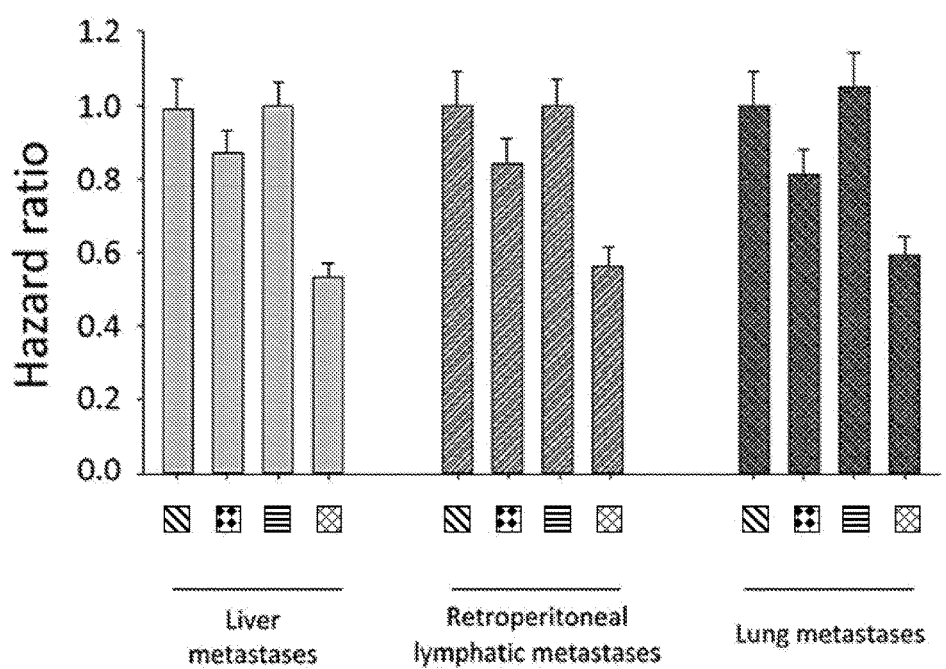

It is known that the presence of lymph node metastases in patients with advanced ovarian cancer indicates a poor prognosis. Currently, except for systematic delivery of Taxol®, there exists no further specific therapy for lymph node metastases, and the role for surgical removal of retroperitoneal lymph nodes as part of maximal cytoreduction is still unclear (E. Halkia, J. Spiliotis, P. Sugarbaker, Diagnosis and management of peritoneal metastases from ovarian cancer, Gastroenterology research and practice, 2012 (2012) 541842). Based on the finding described herein, intraperitoneal delivery of Nano-taxol outperforms systematic delivery of Taxol® in terms of control of lymph node metastases (FIG. 7C). Hazard ratio analysis of overall survival further proves the significant therapeutic effects of regional delivery of Nano-Taxol® to control the metastases to these vital organs (FIG. 7D).

In accordance with the present invention, exemplary paclitaxel nanoparticles show good control of retroperitoneal lymph nodes metastases and liver metastases. For example, in the animal model where mice were induced liver metastases by injection of tumor cells in uterus at d1 and received treatment at day 8, day 11, and day 14, sacrificed at day 18, regional delivery (intraperitoneal) of Nano-Taxol® demonstrated the best control of metastases to retroperitoneal lymph nodes (FIG. 7D).

In some embodiments provide methods for treating cancer via regional delivery in a subject comprising administering to said subject in need thereof an anti-cancer agent (e.g., Nano-taxol, Micelle-taxol) encapsulated in sustained release nanoparticles wherein the anti-cancer agent nanoparticles are administered intrapleurally. In certain embodiments, the cancer is metastasis cancer.

In some embodiments, regional delivery of paclitaxel nanoparticles such as Nano-Taxol exerts more efficient killing of cancer stem cells.

Cancer stem cells (CSCs) are viewed as key tumor-initiating cells that may play an integral role in recurrence. The unique molecular machinery allows for their resistance to most chemotherapies. Depletion of CSCs or inhibition of molecular signature of CSCs may reduce recurrence and improve clinical outcomes (see e.g., Nguyen, et al, "Cancer stem cells: an evolving concept," Nature reviews. Cancer, 12 (2012) 133-143). Cancer cells may also undergo adaptive changes following therapy, exacerbating drug resistance. In epithelial cancers, these adaptive changes may involve, at least in part, epithelial to mesenchymal transitions (EMT). Intriguingly, EMT can trigger reversion to a CSC-like phenotype, providing an association between EMT, CSCs and drug resistance.

Figure 8B:
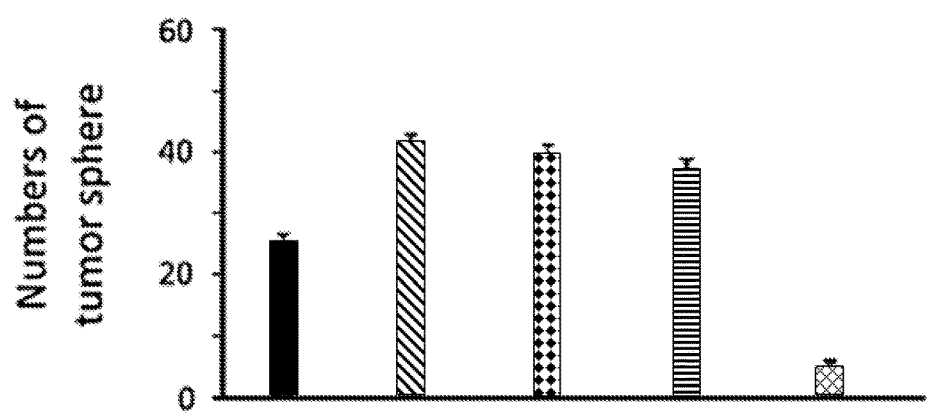
Figure 8C:
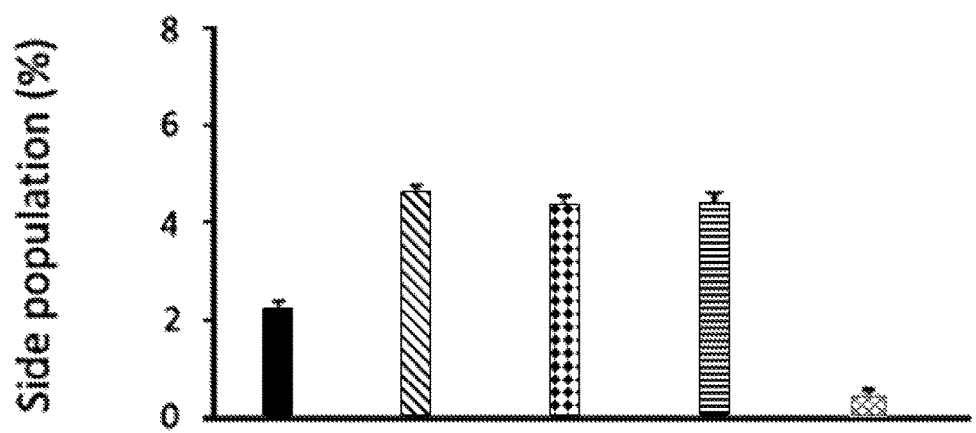
Figure 8D:
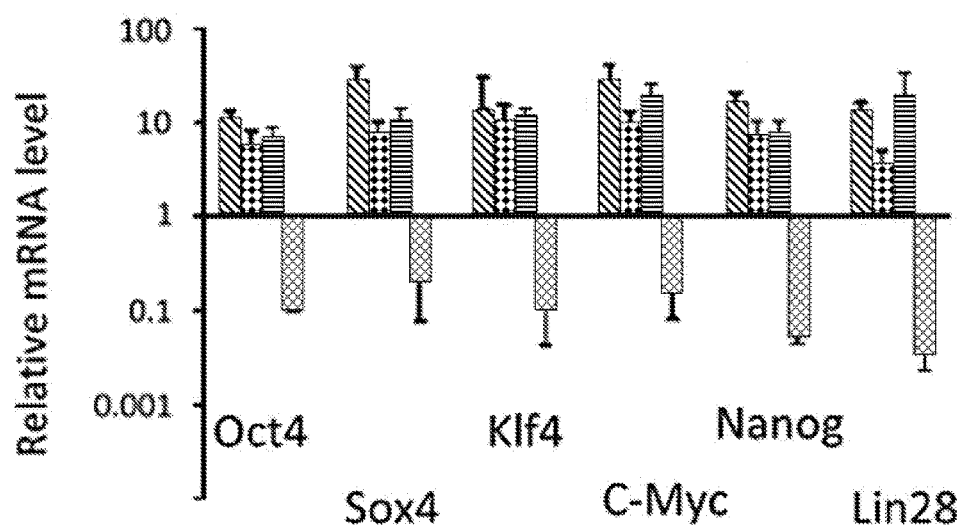
Figure 8E:
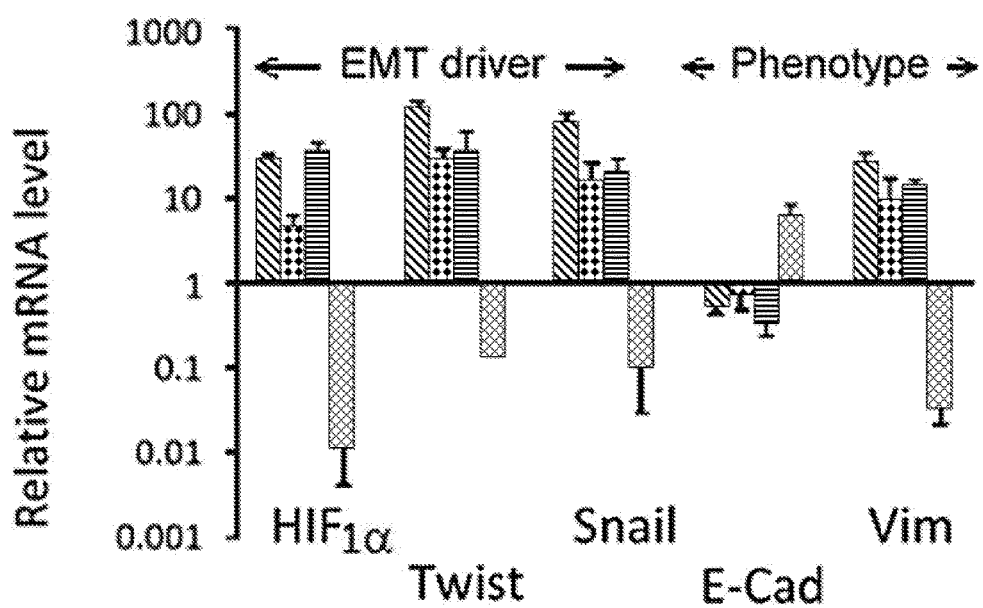
Figure 8F:
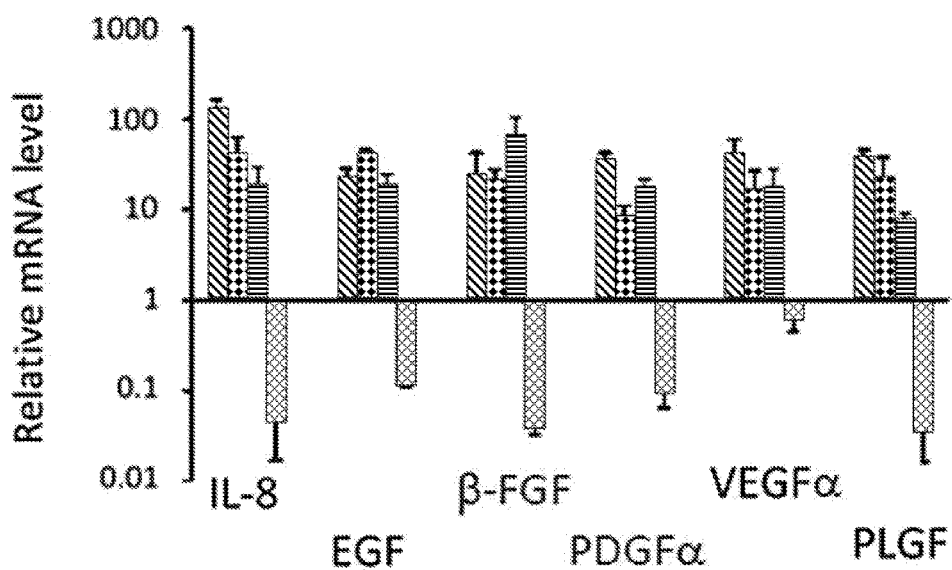
Figure 8G:
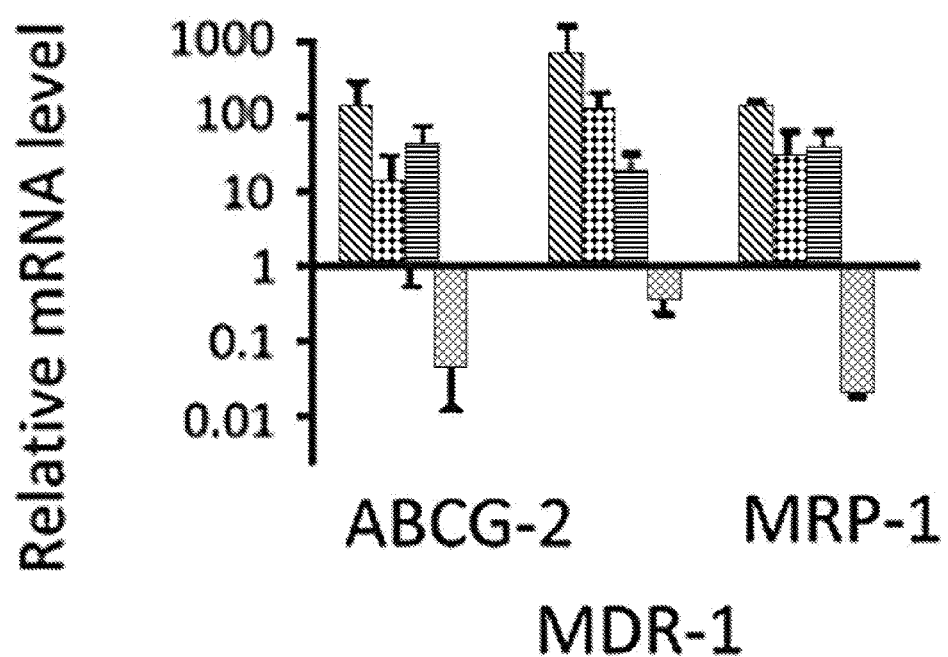
Figure 8H:
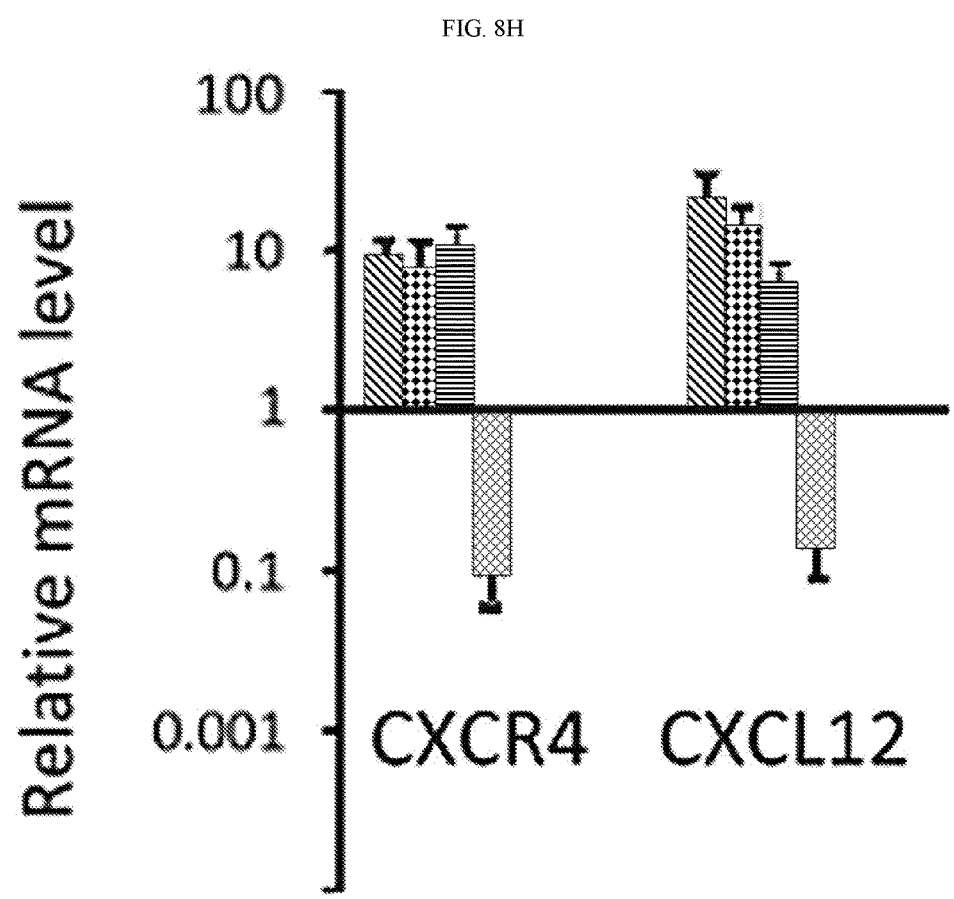

Regional delivery of sustained-released Nano-taxol performed the best for control of tumor sphere formation (FIGS. 8A and 8B) and side population (FIG. 8C). It was also found that both systematic and regional delivery of Taxol® increased the tumor sphere formation and side population, paralleling with others findings, indicating commonly seen increased CSCs in the tumor microenvironment after conventional chemotherapy. Notably, as described herein regional delivery of Nano-taxol overwhelmingly suppressed stemness marker (FIG. 8D), EMT driver and phenotype (FIG. 8E), angiogenesis signal (FIG. 8F), and multidrug resistance signal (FIG. 8G) in the tumor microenvironment.

In some embodiments provides methods of regional delivery of sustained-release nanomedicine wherein said nanomedicine shows equal efficacy to hyperthermia intraperitoneal chemotherapy (HIPEC).

The peritoneal carcinomatosis represents one of the main indication to hyperthermic intraperitoneal chemotherapy (HIPEC) treatment for ovarian cancer. Peritoneal carcinomatosis is also the most frequent form of recurrence (15-40%) in patients with gastric cancer and the second form of recurrence in patients with colon cancer. In some instances, not with to be bound by any particular theories, the most important pharmacologic rationale for combining hyperthermia and chemotherapeutic agent in the peritoneal space is deeper drug penetration. HIPEC has been proved to increase progression-free and overall survival in some studies (see for example, T. D. Yan, D. Black, R. Savady, P. H. Sugarbaker, A systematic review on the efficacy of cytoreductive surgery and perioperative intraperitoneal chemotherapy for pseudomyxoma peritonei, Annals of surgical oncology, 14 (2007) 484-492; T. D. Yan, D. Black, R. Savady, P. H. Sugarbaker, Systematic review on the efficacy of cytoreductive surgery combined with perioperative intraperitoneal chemotherapy for peritoneal carcinomatosis from colorectal carcinoma, Journal of clinical oncology: official journal of the American Society of Clinical Oncology, 24 (2006) 4011-4019). However, HIPEC procedure is time-consuming and requires more effort from nursing and medical staffs and may incur potentially life-threatening complications. The prevalent complications in most series are digestive fistulae, either in the form of anastomotic leak or bowel perforation away from anastomotic lines.

Figure 5D:
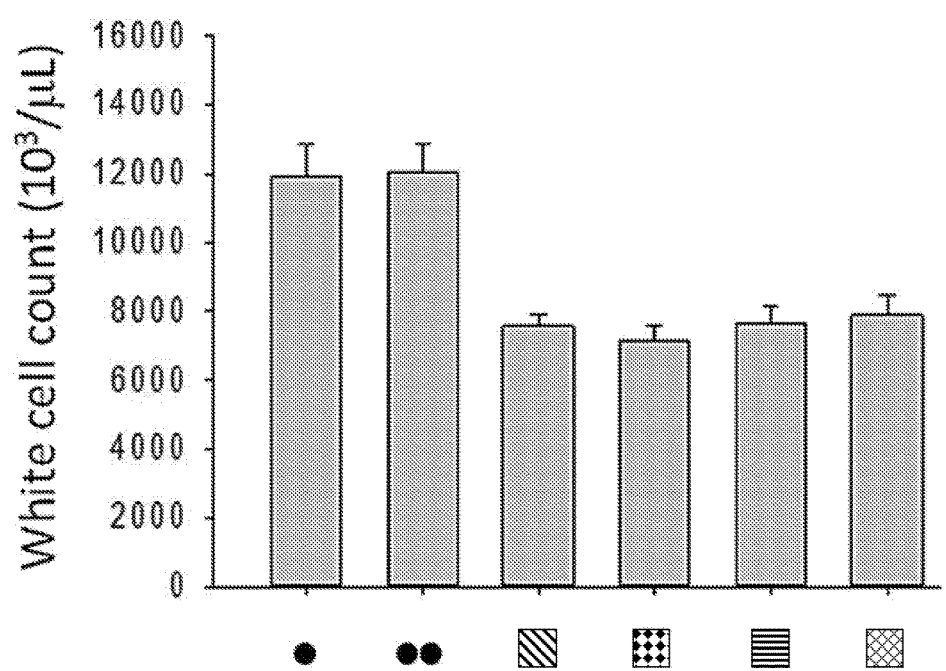
Figure 6A:
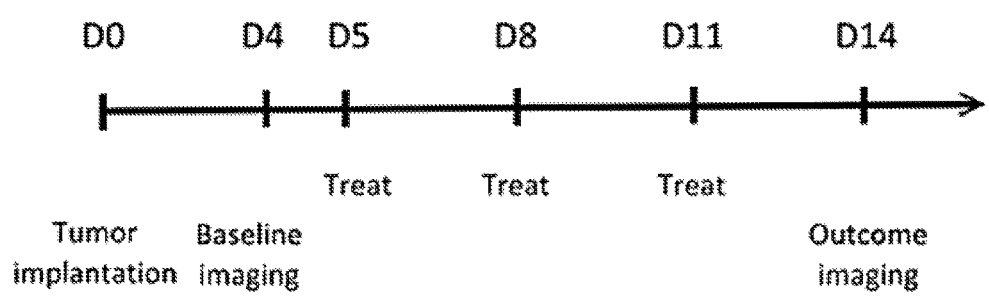
Figure 6C:
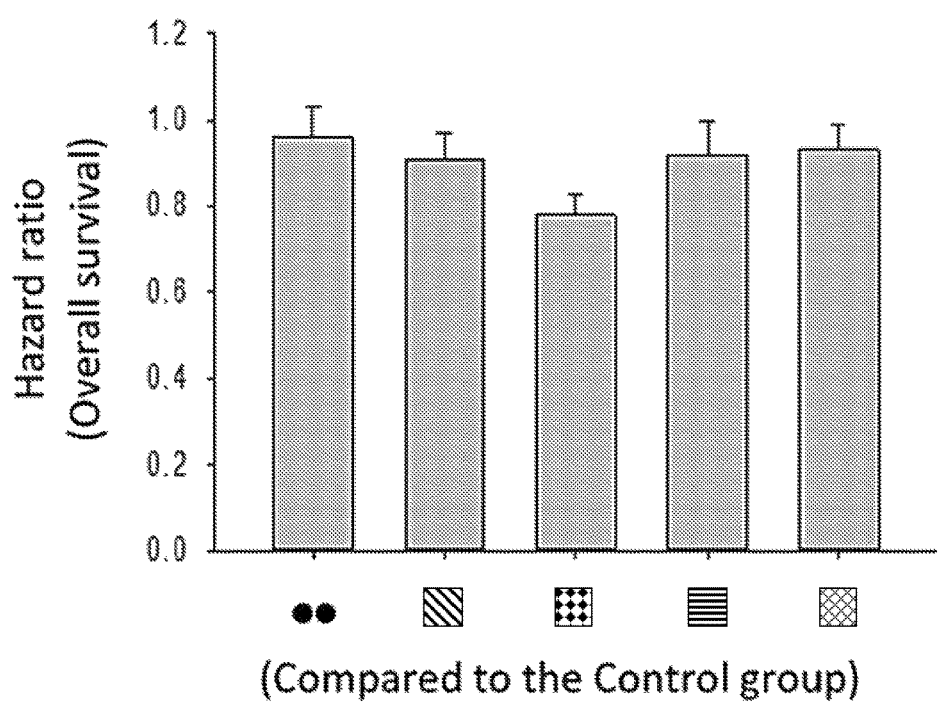
Figure 6D:
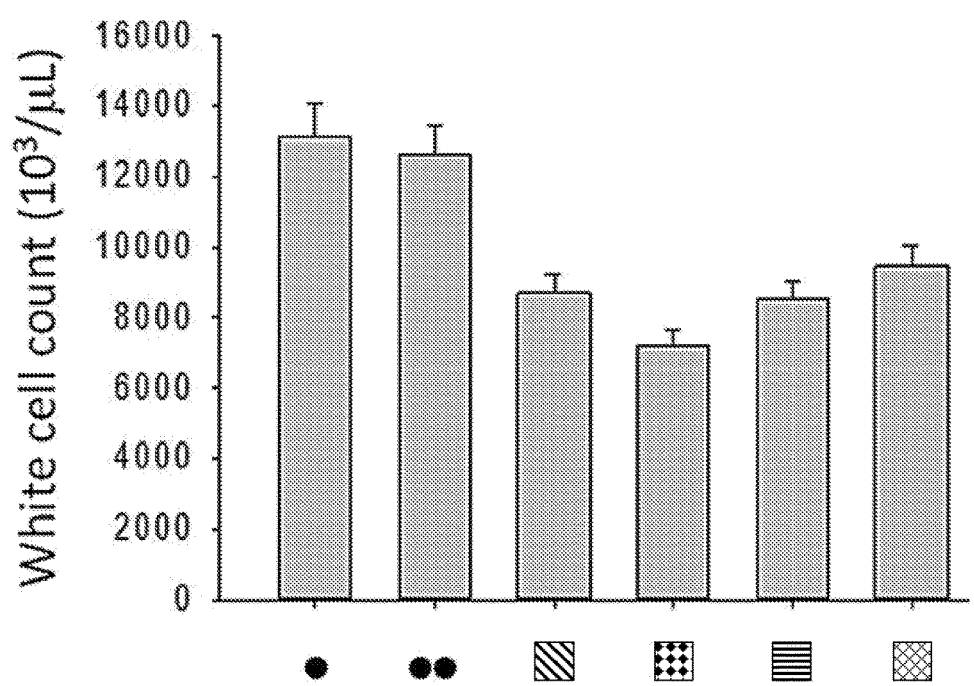
Figure 9A:
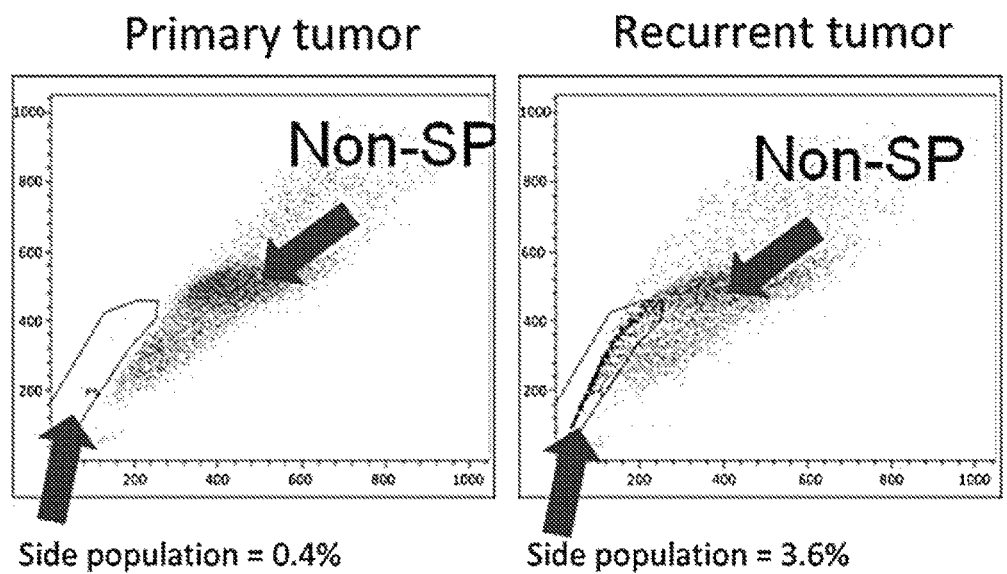
FIG. 9A-D show illustrative results of regional delivery of Nano-Taxol, which can take the place of hyperthermia intraperitoneal chemotherapy. (9A) Recurrent tumors were retrieved and submitted for flow cytometry analysis of Hoechst 33342-stained side population cells. Percentage of side population is significantly higher in the recurrent tumor (3.6%, right panel) than in the primary tumor (0.4%, left panel), indicating that the recurrent tumor harbors more cancer stem cells. (9B) Diagram of hyperthermia intraperitoneal chemotherapy. Depicted are inflow and outflow ports and anal temperature probe to monitor internal temperature of mouse during perfusion. Mice were perfused for 1 h at the rate of 3 mL/min with Taxol® (10 mg/kg). (9C) Both hyperthermia intraperitoneal chemotherapy (HIPEC) of Taxol® and i.p. delivery of Nano-Taxol achieve good tumor control even harboring recurrent tumor cells. (9D) Complications of HIPEC was higher in the HIPEC group presenting with bowel obstruction or perforation. No complications occurred in the i.p. Nano-Taxol group. Experiments were repeated in triplicate.
Figure 9B:
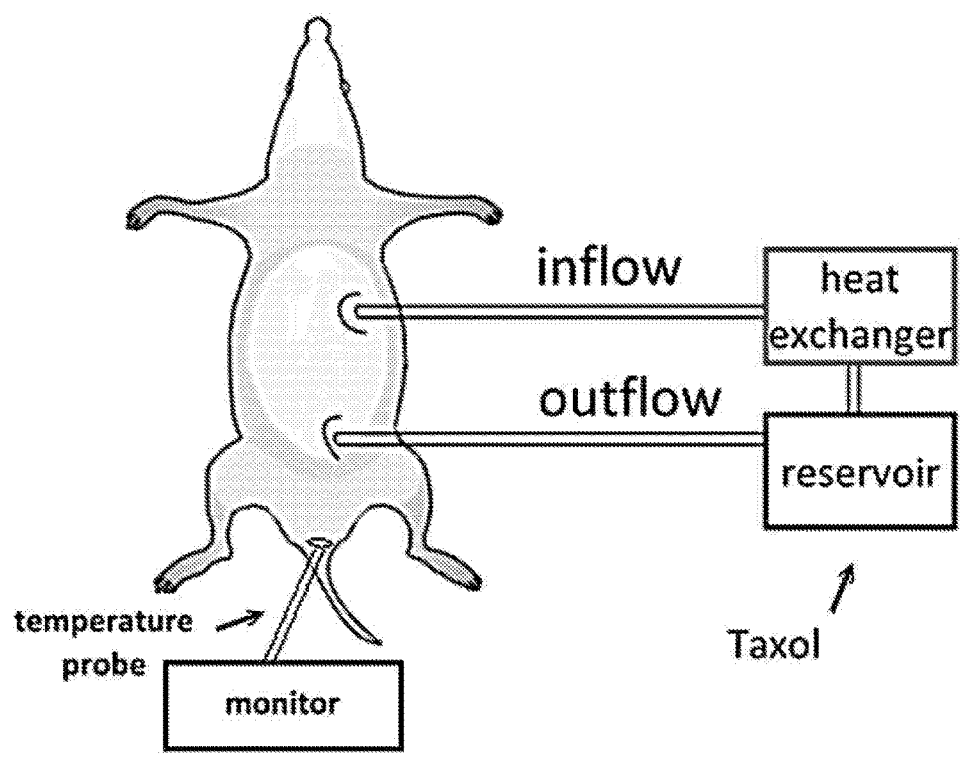
Figure 9C:
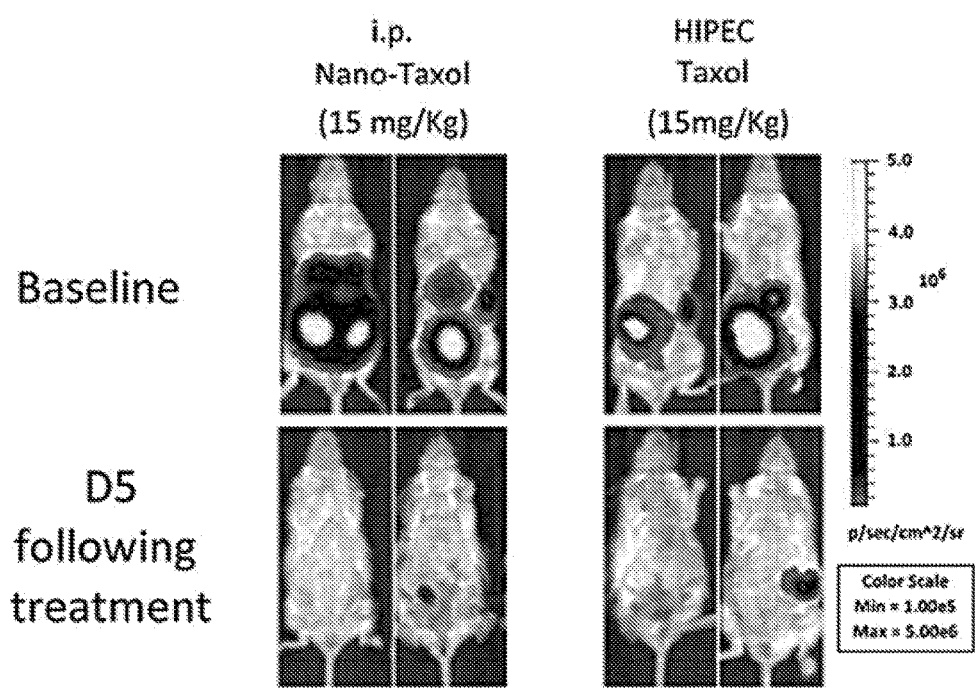
Figure 9D:
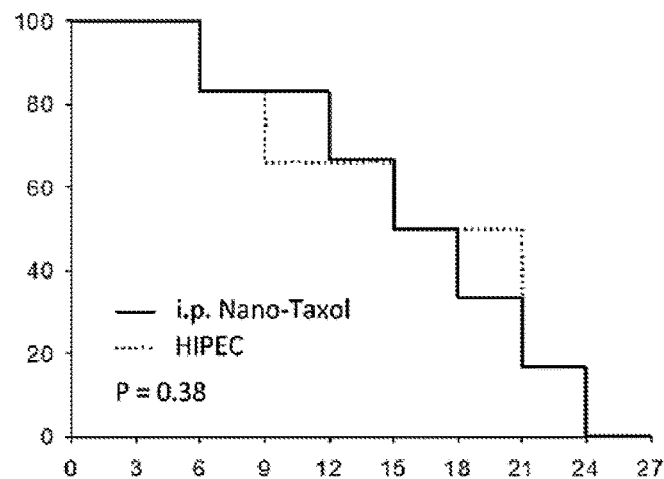

To compare regional delivery of Nano-taxol (which is less time-consuming and less laborious) over HIPEC, a recurrent ovarian cancer model was developed to simulate peritoneal carcinomatosis. Flow cytometry analysis by Hoechst 33342 staining showed higher percentage of side population of recurrent tumor than that of primary tumor (FIG. 9A), indicating more chemoresistance nature of the recurrent tumor. The procedure of HIPEC is depicted (FIG. 9B). It was demonstrated that regional delivery of Nano-taxol and HIPEC has comparable therapeutic efficacy (FIG. 9C), with the former showing less toxic (FIG. 5D). Hence the sustained-release function shows comparable efficacy to hyperthermia.

Based on the description herein, exploiting the EPR effect by systematic delivery of nanomedicine demonstrated poor therapeutic efficacy. Although the EPR effect is a well-established phenomenon in tumor microenvironment, exploiting this effect produces not significant therapeutic efficacy comparing its corresponding free drug on an equidose basis. In contrast, bypassing the EPR effect by regional delivery of nanomedicine (e.g., nanoparticles described herein) by exploiting the sustained-release function, performs far better than systematic delivery in terms of tumor control.

However, not every nanomedicine is suitable for regional delivery.

In accordance with the practice of the present invention, some nanomedicine by regional delivery failed to demonstrate better tumor killing (e.g., Nano-platin, Nano-doxorubicin, and Abraxane® in the current work) is due to the stable interaction (i.e., tight binding) of covalent or non-covalent conjugates of free drug and nanoparticles and thus resulting in not releasing free drug in a timely fashion. For example, the regional delivery of certain nanomedicines, at one extreme, releases free drug too fast, which makes the nanomedicine behave like a free drug (no benefit or effect of nanoparticles); at the other extreme, the nanomedicine releases free drug too slow, resulting in no or less inhibition of tumor growth. Only those nanomedicines, which harbor sustained-release function in a timely fashion, in between the two extremes, can efficiently kill tumor cells (see FIG. 10).

Example 4: Dosage Response Study for Ovarian Cancer Treatment

This study is conducted following the University ethical guidelines on animal experimentation and complied with the Guide for the Care and Use of Laboratory Animals published by the US National Institutes of Health (NIH publication no. 85-23, revised 1996). The animal facility is well controlled for temperature ($22\pm1°$ C.), and humidity ($60\pm5\%$) and a 12 h/12 h light-dark cycle was maintained with access to food and water ad libitum. The study is conducted on 5 week-old female severe combined immunodeficient (SCID) mice treated with Nano-taxol or Micelle-taxol. The cancer cell line ES2/luc is used.

The mice are grouped in accordance with the following table. Each group has 15 mice to collect at least 10 data points.

| Control | Nano-taxol 2 mg/Kg i.p. | Nano-taxol 5 mg/Kg i.p. | Nano-taxol 10 mg/Kg i.p. | Nano-taxol 20 mg/Kg i.p. | Micelle-taxol 10 mg/Kg i.v. | Micelle-taxol 10 mg/Kg i.p. |
|---|---|---|---|---|---|---|
| 15 | 15 | 15 | 15 | 15 | 15 | 15 |

Procedures:

Ovarian cancer is induced onto the mice by a known method. An intraperitoneal injection of ES2/luc ($5\times10^5$-cells in 100 µl HBSS) was performed at Day 0 ($D_0$) when the mice are 6 weeks old. At day 4 ($D_4$) of introduction of cancer cells, IVIS® spectrum is measured for each mouse to assess tumor cell growth. At day 8 ($D_8$) and day 11 ($D_{11}$), different dosages of Nano-taxol and Micelle-taxol are used to treat the mice in accordance with the table above.

At day 14 ($D_{14}$), IVIS® spectrum is used to measure tumor cell growth again for each mouse to evaluate the treatment of each mouse. The surviving rate of each group will be continued monitoring.

Example 5: Colon Cancer and Gastric Cancer Experiment

This study is conducted following the University ethical guidelines on animal experimentation and complied with the Guide for the Care and Use of Laboratory Animals published by the US National Institutes of Health (NIH publication no. 85-23, revised 1996). The study is conducted on 5 week-old female SCID mice treated with Nano-taxol or Micelle-taxol. The cancer cell lines HT-29-luc (colon cancer cell line) and NCI-N87-luc 2-GFP (gastric cancer cell line) are used.

The mice are grouped in accordance with the following table. Each group has 15 mice to collect at least 10 data points.

| HT-29-luc | NCI-N87-luc 2-GFP |
|---|---|
| 15 | 15 |

Procedures:

Colon and gastric cancers are induced onto the mice by known methods. An intraperitoneal injection of HT-29-luc or NCI-N87-luc 2-GFP cell lines ($1\times10^6$-cells in 100 µl HBSS) was performed at Day 0 ($D_0$) when the mice are 6 weeks old. At suitable timing, e.g, day 4 ($D_4$) of introduction of cancer cells, IVIS® spectrum (via in vitro image system) is measured for each mouse. At second suitable timings, e.g., day 8 ($D_8$) and day 11 ($D_{11}$), different dosage of Nano-taxol and Micelle-taxol are used to treat the mice in accordance with the table above.

At day 14 ($D_{14}$) or other suitable time, IVIS® spectrum is measured again for each mouse and the mice are evaluated for the treatments of colon or gastric cancer. The surviving rate of each group will be continued monitoring.

Example 6: Colon Cancer Treatment Comparison Between Nano-Taxol and Free Paclitaxel This study is conducted following the University ethical guidelines on animal experimentation and complied with the Guide for the Care and Use of Laboratory Animals published by the US National Institutes of Health (NIH publication no. 85-23, revised 1996). The study is conducted on 5 week-old female SCID mice treated with Nano-taxol or free paclitaxel. The cancer cell line HT-29-luc (colon cancer cell line) is used.

The mice are grouped in accordance with the following table (total of 5 groups). Each group has 15 mice to collect at least 10 data points.

| Control | Nano-taxol 10 mg/Kg i.v. | Nano-taxol 10 mg/Kg i.p. | paclitaxel 10 mg/Kg i.v. | paclitaxel 10 mg/Kg i.p. |
|---|---|---|---|---|
| 15 | 15 | 15 | 15 | 15 |

Colon cancer tumor is induced onto the mice by known method. An intraperitoneal injection of HT-29-luc cell line ($1\times10^6$-cells in 100 µl HBSS) was performed at Day 0 ($D_0$) when the mice are 6 weeks old. At suitable timing, e.g, day 11 ($D_{11}$) of introduction of cancer cells, IVIS® spectrum is measured for each mouse. Mice treated with 10 mg/kg Nano-taxol or paclitaxel by different drug delivery pathway (i.p. or i.v.) at Day 12 ($D_{12}$), Day 15 ($D_{15}$) and Day 18 ($D_{18}$). After 21 days ($D_{21}$), the effectiveness of Nano-taxol or paclitaxel is assessed of tumor cell growth by IVIS system. The survival of mice is recorded.

Example 7: Evaluation the Antitumor Activity of Nano-Taxol and Micelle-Taxol in Ovarian Cancer Xenograft Mice Model Epithelial ovarian cancer is the second most common gynecologic malignancies and the leading cause of death from gynecologic cancers in the United States. In 2014, an estimated 21,980 new cases of ovarian cancer and 14,270 deaths from ovarian cancer will occur in the United States (2014 American Cancer Society). Most patients with ovarian cancer present with either stage III or stage IV disease at their first visit in clinic. In Taiwan, according to the reports from NHRI (2011), there were estimated 1000 new cases of ovarian cancer per year.

Regional chemotherapy, such as intraperitoneal chemotherapy, has the pharmacokinetic advantage of an increased ratio of the peritoneal-to-plasma area under the curve to the tumor-containing peritoneal cavity (Lancet Oncol. 2003; Nat Rev Clin Oncol. 2010). Despite this pharmacokinetic advantage, the clinical use of intraperitoneal therapy has been challenged by the premature clearance of a small-molecular-weight drug from the peritoneal cavity, a lack of target specificity, and poor drug penetration into the target tissues (Nat Rev Cancer. 2006). Theoretically, the drawbacks associated with intraperitoneal chemotherapy of anticancer agents could be overcome by the incorporation of a drug into special designed delivery matrices, which facilitate sustained drug release. Sustained release of a drug in peritoneal cavity would lead to enhanced cell exposure to anticancer agent for prolonged periods and would likely result in an effective cell killing. Tamura and coworkers observed that, in peritoneal tumor bearing mice, the intraperitoneal administration of anticancer drugs in poly(D,L- lactic acid) microspheres induced sustained tumor growth inhibition along with prolonged survival time (Eur J Pharm Biopharm. 2002).

This study aims to investigate different doses of Nano-Taxol and Micelle-taxol by i.p. or i.v. for the treatment of ovarian cancer using xenograft tumor mice model.

Study Design:

To assess if these nanoparticle medicines are effective in the treatment of intraperitoneal disseminated ovarian cancer, ES2-luc cells were inoculated into peritoneal cavity via intraperitoneal injection (i.p.) in SCID mice. Tumor cell growth was determined by measuring bioluminescence images (BLI) using IVIS system. Treatments were initiated when the tumor dissemination (judged by luminescence activity) reached baseline. Mice were treated with 2, 5, 10 and 20 mg/kg Nano-taxol by i.p. or 10 mg/kg Micelle-taxol by i.v. and i.p. once every 3 days for 3 doses. On Day 14 (D14), the antitumor activity of Nano-taxol or Micelle-taxol was assessed by the reduction of BLI. Survival of these animals was recorded.

Experimental Procedures

The indicated ES2-luc cell numbers were seeded in 24 wells dish at 37° C. for 24 hrs. BLI were captured after 24 hrs by IVIS-50 system. The correlation between luminescence activity and cell growth was showed in FIG. 11.

Five-week-old female SCID mice (CB.17 SCID/SCID) were purchased from the National Laboratory Animal Breeding and Research Center of Taipei and maintained in the oncology animal facility of Taipei Veterans General Hospital, Taipei, Taiwan. The animals were used in compliance with the institutional animal health care regulations.

SCID mice (6 weeks) were injected with $5 \times 10^5$ ES2-luc cells in 100 ul opti-MEM by i.p. on Day 0 (D0). After 4 days (D4), tumor cell growth was determined by measuring BLI using IVIS system (baseline). Control group was given 100 ul of 0.9% Sodium Chloride Injection. Each group BLI was normalized before treatment. Mice were treated with vehicle, Nano-taxol at 2, 5, 10 and 20 mg/kg by i.p., and Micelle-taxol at 10 mg/kg by i.v. and i.p. on Day 5 (D5), Day 8 (D8), and Day 11 (D11). On Day 14 (D14), the antitumor activity of Nano-taxol or Micelle-taxol was assessed by the reduction of BLI. Animals were monitored individually till death for survival evaluation.

Bioluminescence Images (BLI) Measurement

The mice were imaged with the IVIS-50 system (Xenogen, Alameda, Calif.). The mice were implanted with ES2-luc cells ($5 \times 10^5$/mouse) on Day 1. BLI were captured on indicated days. One mouse died at Day 17. The correlation between bioluminescence images (BLI) and cell growth in animal was showed in FIG. 12A-B.

Statistical Analysis

The results are given as the mean±standard deviation of at least three experiments. Overall survival was defined as the time from the date of tumor implantation to the date of death and is presented as the Kaplan-Meier survival curve.

Tumor Growth Assessment

Figure 13:
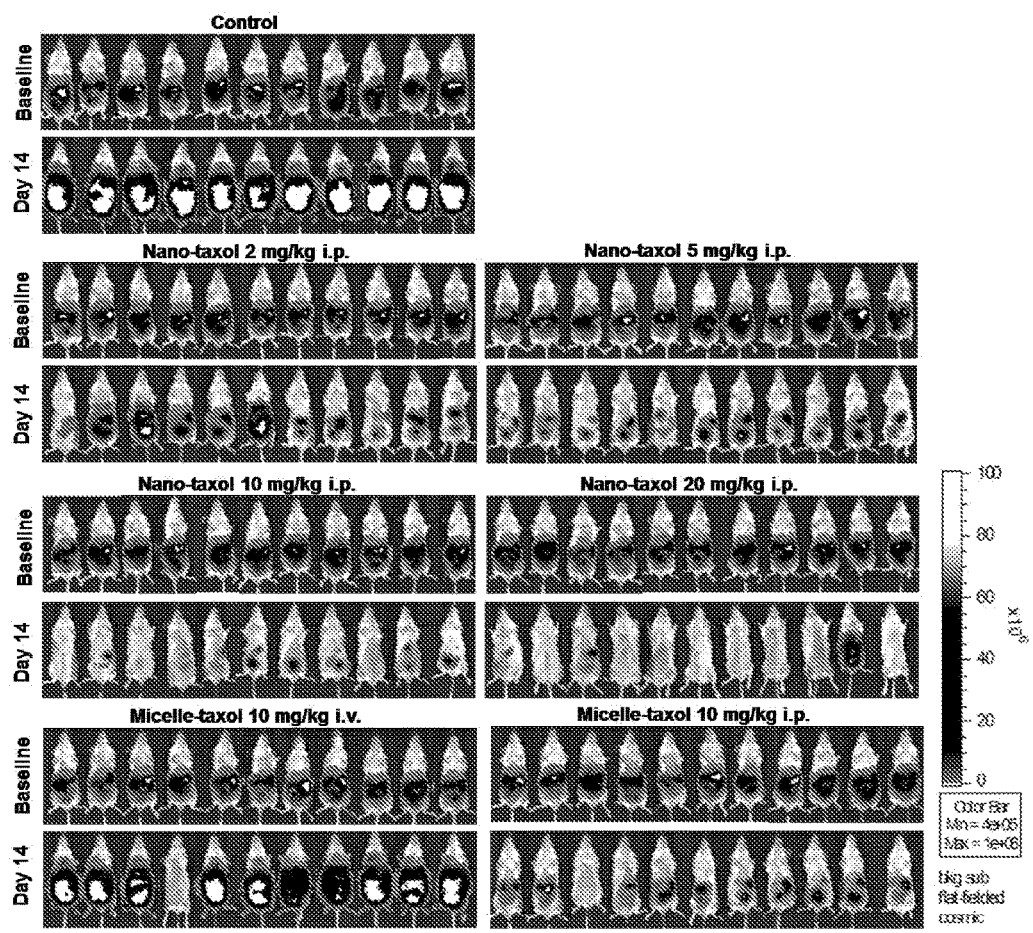
FIG. 13 show illustrative results of the tumor growth inhibition by Nano-taxol or Micelle-taxol. The mice were inoculated with ES2-luc cells ($5\times10^5$/mouse) on Day 1 and were treated on Day 5, Day 8, and Day 11 with the indicated doses of Nano-taxol or Micelle-taxol. BLI were captured on Day 4 (baseline) and Day 14. One mouse died following i.v. and i.p. of Micelle-taxol before IVIS analysis.
Figure 14:
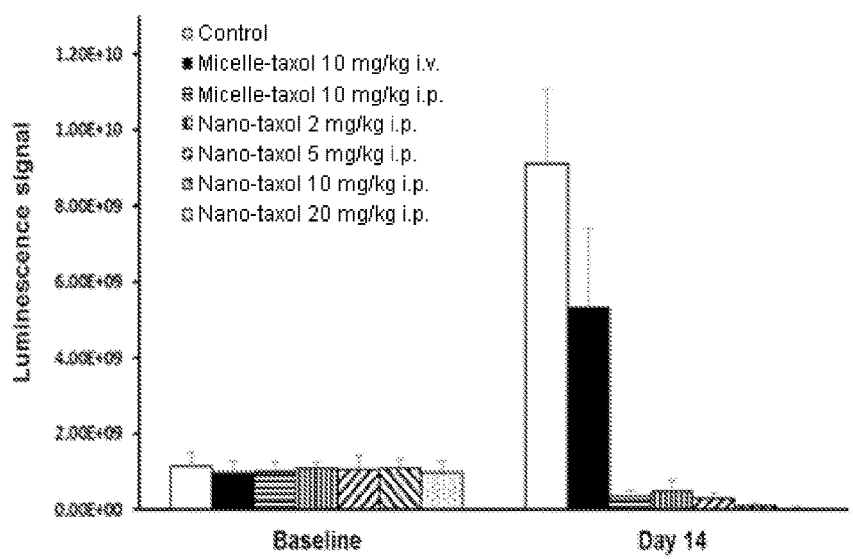
FIG. 14 provides quantification of BLI results of FIG. 13 using the Xenogen IVIS-50 and Living Image software (Caliper Life Sciences). Data was presented as mean±SD, N=11 (Nano-taxol), N=10 (Micelle-taxol).

Following i.p. injection, Nano-taxol inhibited ovarian tumor growth in a dose-dependent manner (FIG. 13 and FIG. 14). Nano-taxol at 20 mg/kg almost completely eradicated ovarian cancer in the peritoneal cavity in 8 out of 11 mice (FIG. 13). Reduced tumor burden by greater than 50% in 2/11 mice. Nano-taxol at 10 mg/kg eradicated tumors in the peritoneal cavity in 3 of 11 mice (FIG. 13) and reduced tumor burden by greater than 50% in 8/11 mice. Nano-taxol at 2 mg/kg and at 5 mg/kg also had anti-tumor activity compared with Control (FIG. 13). Tumor growth inhibition (TGI) reached 100% at 20 mg/kg and greater than 95% at 2 mg/kg (FIG. 13 and FIG. 14). Micelle-taxol also inhibited ovarian cancer ES2 cells growth following i.p. but not i.v. TGI was 98% after i.p. administration (FIG. 13 and FIG. 14).

To confirm the tumor inhibition effect of Micelle-taxol and Nano-taxol following i.p. injection again, $2^{nd}$ experiment (FIG. 15A-B) was performed, and the schedule was the same as above. Following i.p. injection, Nano-taxol and Micelle-taxol inhibited ovarian tumor growth. Nano-taxol at 10 mg/kg eradicated tumors in the peritoneal cavity in 2 of 7 mice and reduced tumor burden in 5/7 mice. Similar results were found with Micelle-taxol treatment. The TGI reached nearly 100% in 10 mg/kg Nano-taxol and 10 mg/kg Micelle-taxol i.p. treatment mice (FIG. 15A-B).

Figure 17:
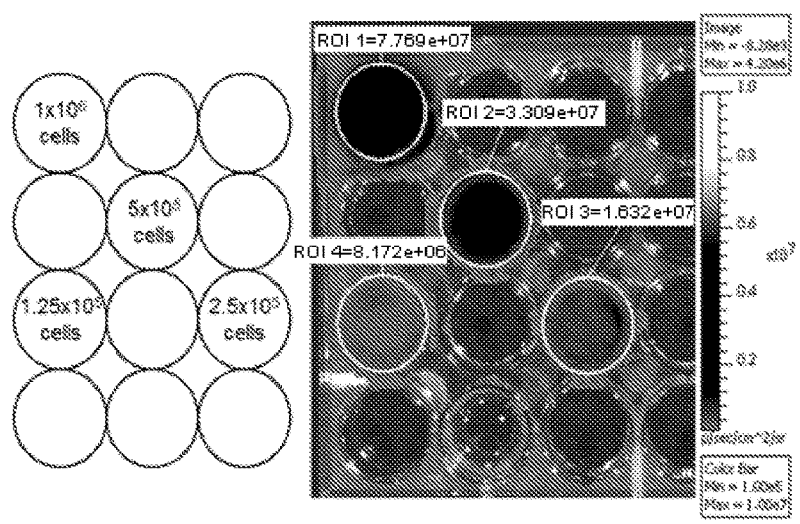
FIG. 17 shows illustrative ascetic cancer cells using IVIS system. Ascites from the mouse in control group as in FIG. 16A was collected and subjected to cell culture. The cultured cells were then analyzed using IVIS system. The cells showed BLI signal, demonstrating that the ascites contained human ovarian cancer ES2-luc cells.

To demonstrate the luminescence was resulted from ES2-luc cells, mice were dissected on the day of death. As shown in FIG. 16, one mouse receiving control (16A) and one mouse receiving Micelle-taxol by i.v. (16B) had the most severe ascites. Ascites from the control mice (16A) was collected and subjected to cell culture. The cultured cells were then analyzed using IVIS system. The cells showed BLI, demonstrating that the ascites contained human ovarian cancer ES2-luc cells (FIG. 17). After treatment with Micelle-taxol or Nano-taxol by i.p. (FIGS. 16C to 16G), less ascites were found as the dose increase.

Figure 18:
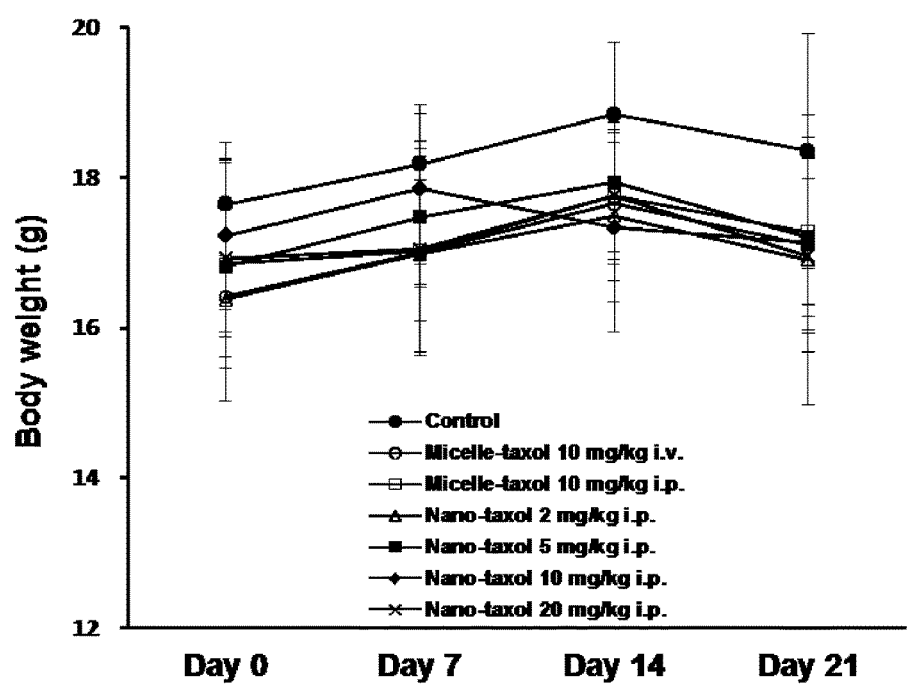
FIG. 18 shows illustrative results of the mice body weight of the animal study associated with FIG. 17.

All treatments in the study did not significantly alter body weight of animals as shown in FIG. 18.

Survival Assessment

Figure 19:
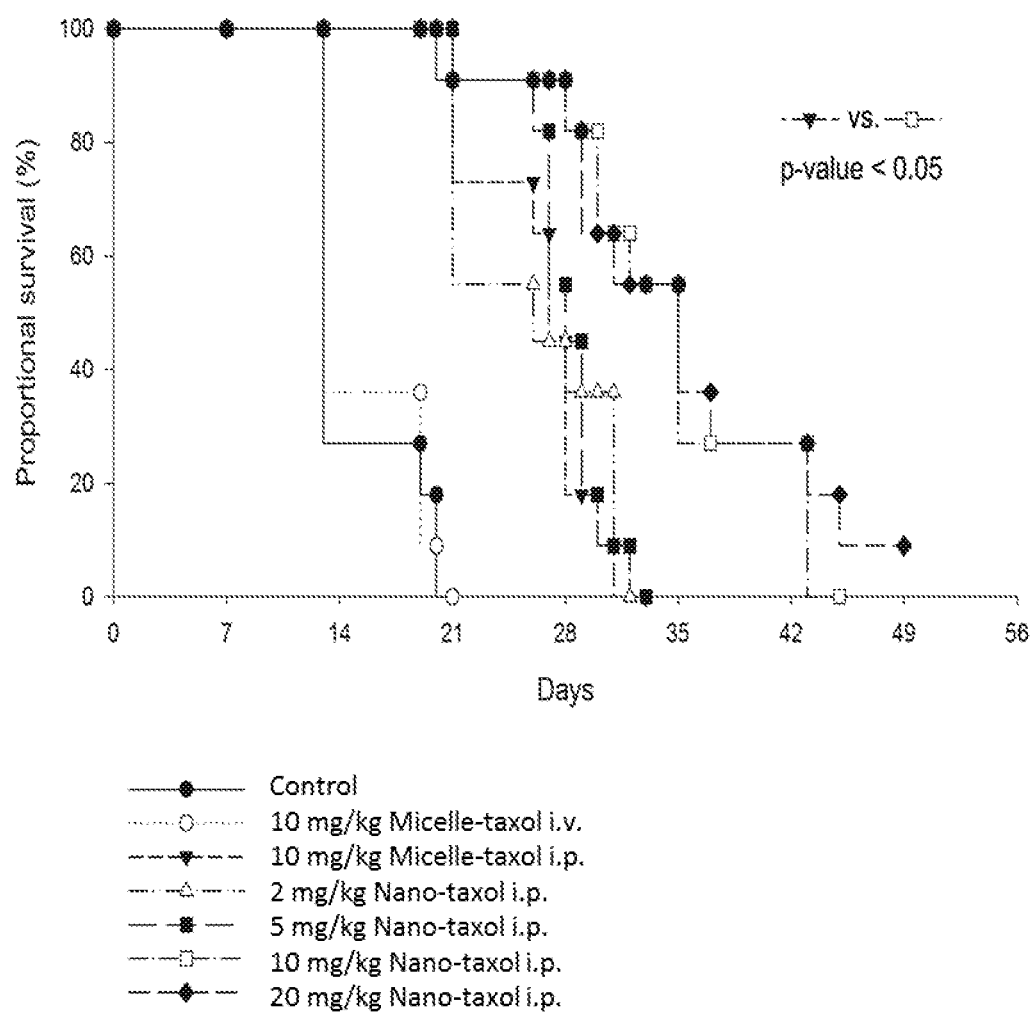
FIG. 19 shows illustrative results of the survival of the ES2-luc i.p. injected mouse model after treatment with Micelle-taxol or Nano-taxol. ES2-luc cells ($5 \times 10^5$ cells) were inoculated into the peritoneal cavity of mice on Day 1. Saline as the vehicle control (●), Micelle-taxol i.v. (10 mg/kg: ○), Micelle-taxol i.p. (10 mg/kg: ▼), Nano-taxol i.p. (2 mg/kg: Δ), Nano-taxol i.p. (5 mg/kg: ■), Nano-taxol i.p. (10 mg/kg: □) or Nano-taxol i.p. (20 mg/kg: ◆) was administered on Days 5, 8 and 11, and the survival duration was analyzed (n=11, Nano-taxol group; n=10, Micelle-taxol group). This survival based on FIG. 13 mice.

The survival duration was 21 days in the control mice after the inoculation of $5 \times 10^5$ ES2-luc cells (see FIG. 19). Following i.v. administration of 10 mg/kg Micelle-taxol, survival duration was 21 days. Following i.p. administration of Micelle-taxol at 10 mg/kg, Nano-taxol at 2, 5, 10 and 20 mg/kg, survival duration was 33, 32, 33, 45 and over 49 days, respectively (FIG. 19). IP administration of both Nano-taxol and Micelle-taxol prolonged the survival duration over 12 days compared with control group, but the difference was only significant between control group and Nano-taxol treatment groups at 5, 10 and 20 mg/kg ($p<0.05$). Intraperitoneal administration of 10 mg/kg and 20 mg/kg Nano-taxol significantly prolonged the survival duration by 12 days compared with 10 mg/kg Micelle-taxol i.p. ($p<0.05$) (FIG. 19).

The median survival day of control and 10 mg/kg Micelle-taxol i.v. group was 19 days. Following i.p. administration of Micelle-taxol at 10 mg/kg, Nano-taxol at 2, 5, 10 and 20 mg/kg, median survival day was 28, 27, 29, 37 and 37 days, respectively (FIG. 19).

Figure 20:
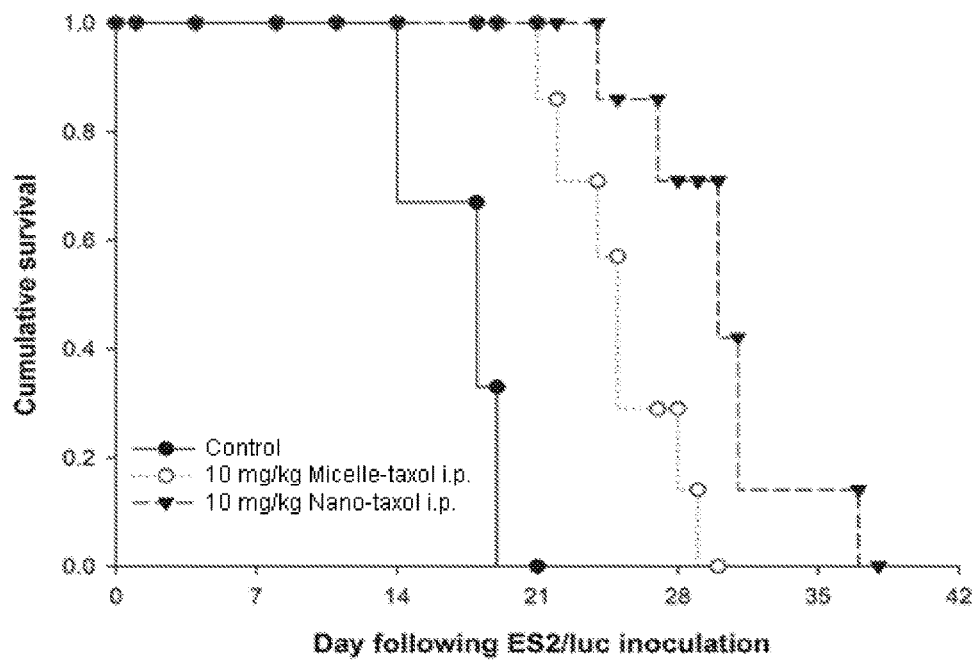
FIG. 20 shows illustrative results of the survival of the ES2-luc i.p. injected mouse model after treatment with 10 mg/kg Micelle-taxol or Nano-taxol. ES2-luc cells ($5 \times 10^5$ cells) were inoculated into the peritoneal cavity of mice on day 1. Saline as the vehicle control (●), Micelle-taxol i.p. (10 mg/kg: ○), Nano-taxol i.p. (10 mg/kg: ▼) was administered on days 5, 8 and 11, and the survival duration was analyzed (control group, n=3; Micelle-taxol and Nano-taxol group, n=7). This survival data is based on the results of FIG. 15 mice.

In the follow up experiment, the survival duration was 19 days in the control mice after the inoculation of $5 \times 10^5$ ES2-luc cells. Following i.p. administration of 10 mg/kg Micelle-taxol and 10 mg/kg Nano-taxol, survival duration was 30 and 38 days, respectively (FIG. 20). Both Nano-taxol i.p. and Micelle-taxol i.p. prolonged the survival duration over 11 days compared with control group ($p<0.05$). 10 mg/kg Nano-taxol i.p. significantly prolonged the survival duration by 8 days compared with 10 mg/kg Micelle-taxol i.p. ($p<0.05$) (FIG. 20).

The median survival day of control, 10 mg/kg Micelle-taxol i.p. and 10 mg/kg Nano-Taxol i.p. was 18, 27 and 31 days, respectively (FIG. 20).

Conclusion

Both Nano-taxol and Micelle-taxol after i.p. administration had antitumor activity. Nano-taxol showed dose-dependent antitumor activity and almost completely eradicated ovarian cancer in the peritoneal cavity in 8 out of 11 mice at 20 mg/kg. At 10 mg/kg, tumor eradication was found in 3 of 11 mice and reduced tumor burden in 8 of 11 mice. The response rate was 100%. Therefore, 10 mg/kg was considered to be the minimum effective dose.

Thus it is clearly shown that both Nano-taxol and Micelle-taxol can treat ovarian cancer intraperitoneally.

Example 8: Evaluation the Antitumor Activity of Nano-Taxol in Colon Cancer Syngeneic Mice Model To assess the effectiveness of Nano-taxol in the treatment of intraperitoneal disseminated colon cancer, CT-26-luc cells were inoculated into peritoneal cavity via intraperitoneal injection (i.p.) in BALB/c mice. Tumor cell growth was determined by measuring bioluminescence images (BLI) using IVIS system. Treatments were initiated when the tumor dissemination (judged by luminescence activity) reached baseline. Mice were treated with 10 mg/kg Nano-taxol by i.v. and i.p., or 10 mg/kg Paclitaxel (PTX) by i.v. and i.p. once every 2 days for 3 doses. On Day 11 (D11), the antitumor activity of Nano-taxol or PTX was assessed by the reduction of BLI. Survival of these animals was recorded.

Figure 21:
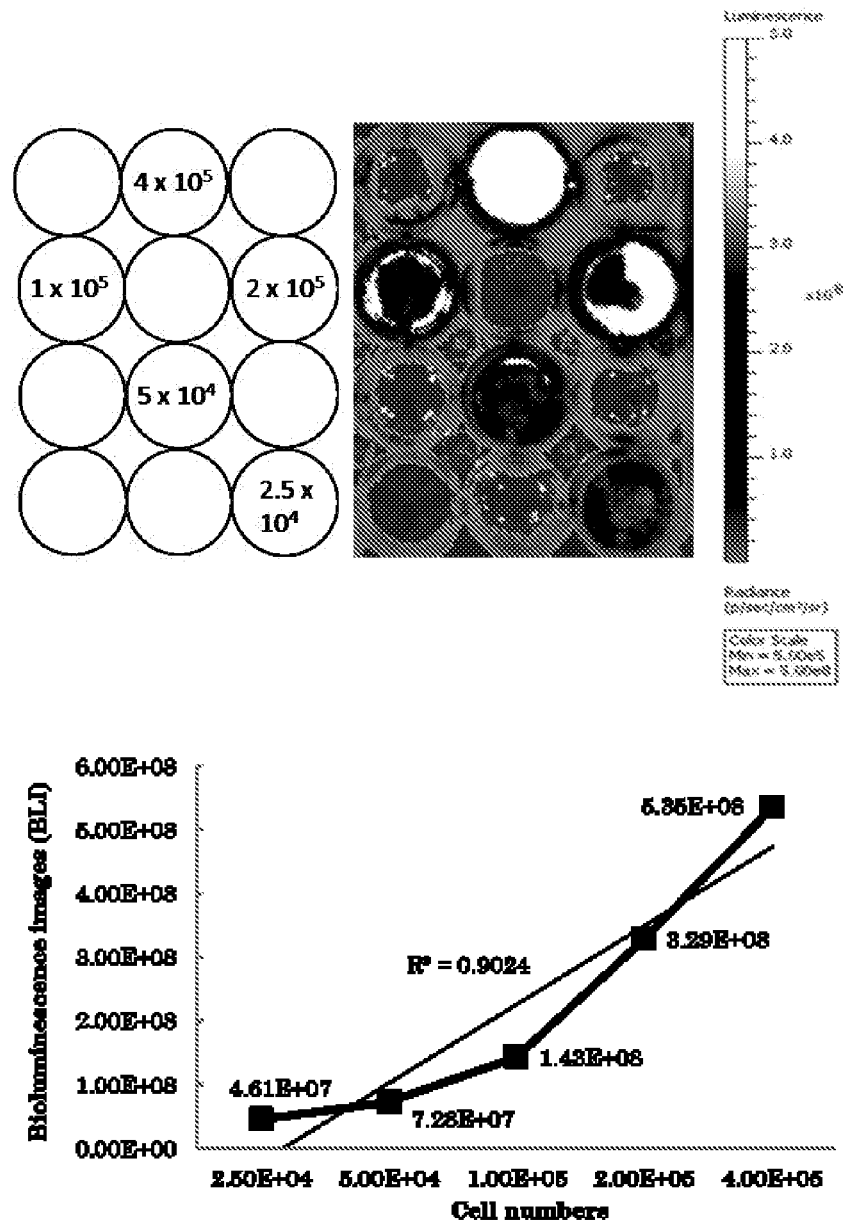
FIG. 21 shows the correlation between BLI and cell growth in vitro. CT-26-luc cells were seeded at the indicated numbers in 24-wells dish at 37° C. for 24 hrs. Bioluminescence images were captured after 24 hrs by IVIS-50 system.

CT-26-luc cells were seeded at the indicated numbers in 24-wells dish at 37° C. for 24 hrs. Bioluminescence images were captured after 24 hrs by IVIS-50 system. The correlation between luminescence activity and cell growth was showed in FIG. 21.

Preparation

Five-week-old female BALB/c mice were purchased from the National Laboratory Animal Breeding and Research Center of Taipei and maintained in the oncology animal facility of Taipei Veterans General Hospital, Taipei, Taiwan. The animals were used in compliance with the institutional animal health care regulations, and all of the animal experimental procedures were approved by the Institutional Animal Care and Use Committee.

Each mouse was given about 100 ul (i.v.) and 200 ul (i.p.) Nano-taxol or PTX at indicated concentrations. Exact dosing volume was calculated using body weight. Control group was given 100 ul of 0.9% Sodium Chloride Injection.

BALB/c mice (6 weeks) were injected with $1 \times 10^5$ CT-26-luc cells in 250 ul opti-MEM by i.p. on Day 0 (D0). After 4 days (D4), tumor cell growth was determined by measuring luminescence activity using IVIS system (baseline). Each group Bioluminescence images (BLI) was normalized by average BLI of total mice before treatment. Mice were treated with vehicle, Nano-taxol at 10 mg/kg by i.p. and i.v., and PTX at 10 mg/kg by i.p. and i.v. On Day 4 (D4), Day 6 (D6), and Day 8 (D8). On Day 11 (D11), the antitumor activity of Nano-taxol or PTX was assessed by the reduction of luminescence activity. Animals were monitored individually till death for survival evaluation.

The mice were imaged with the IVIS-50 system (Xenogen, Alameda, Calif.). The correlation between bioluminescence images (BLI) and cell growth in animal was showed in FIG. 22A-B.

Statistical Analysis: The results are given as the mean±standard deviation of at least three experiments. Overall survival was defined as the time from the date of tumor implantation to the date of death and is presented as the Kaplan-Meier survival curve.

Results and Conclusion

Figure 23A:
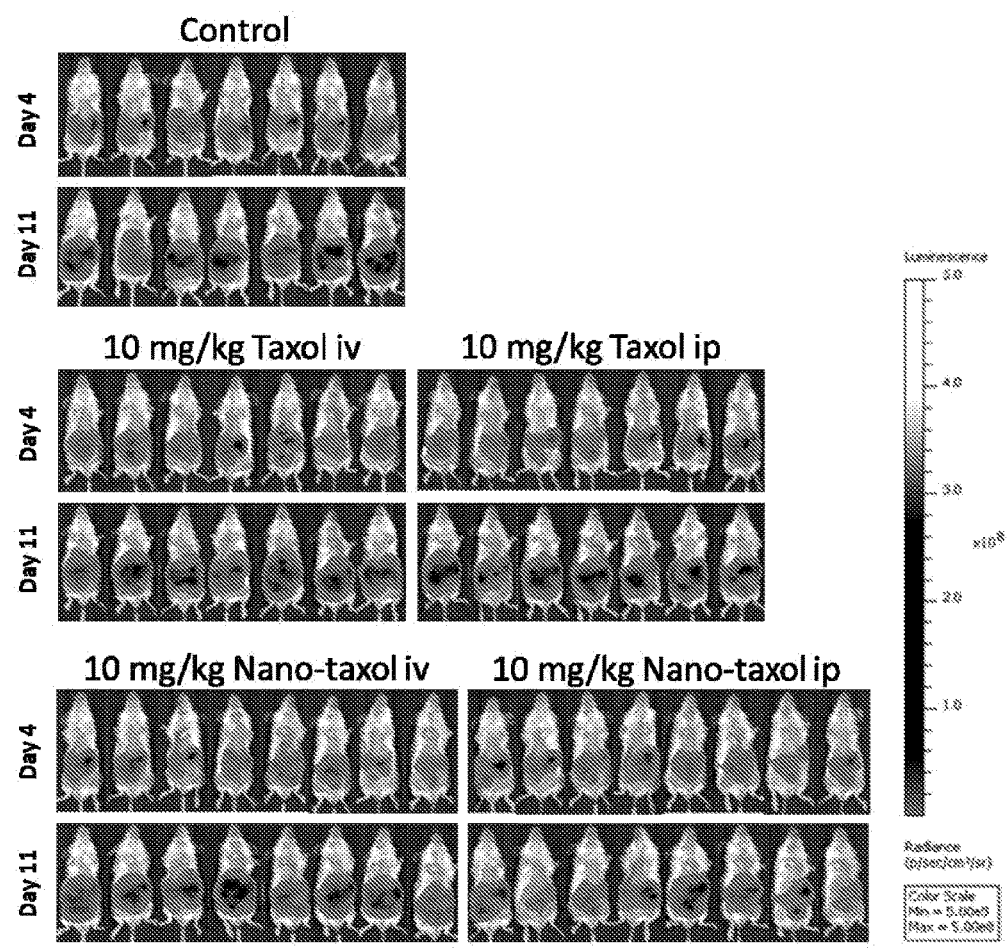
FIG. 23A shows illustrative results of the tumor growth inhibition by Nano-taxol or PTX. The mice were inoculated with CT-26-luc cells ($1 \times 10^5$/mouse) on Day 1 and were treated on Day 4, Day 6, and Day 8 with the indicated doses of Nano-taxol or PTX. Bioluminescence images were captured on Day 4 (baseline) and Day 14.
Figure 23B:
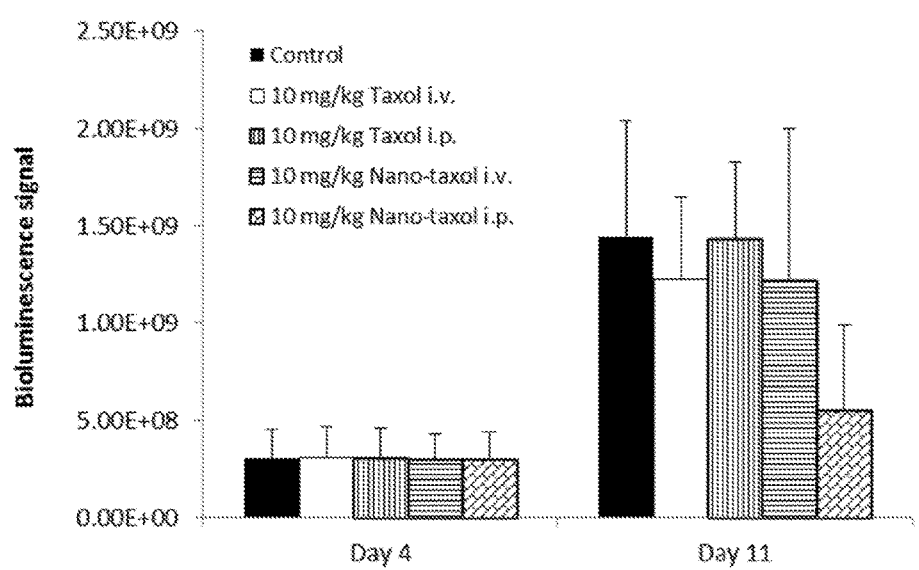
FIG. 23B provides quantification of BLI results of FIG. 23A using the Xenogen IVIS-50 and Living Image software (Caliper Life Sciences). Data was presented as mean±SD, N=8 (Nano-taxol), N=7 (PTX and Control).

Tumor Growth Assessment:

To evaluate the effect of Nano-taxol in colon cancer, a disseminated colon cancer syngeneic model was established. The correlation between the BLI and the CT-26-luc cell growth in BALB/c mice showed in FIGS. 22A-B. Following i.p. injection, Nano-taxol inhibited colon tumor growth following i.p. but not i.v. (FIG. 23A-B). Nano-taxol at 10 mg/kg i.p. reduced tumor burden by 75% in 6 of 8 mice but no tumor eradication was found (FIG. 23B). In addition, PTX did not inhibit colon tumor growth following i.p. and i.v. as shown in both FIG. 23A-B.

Figure 24:
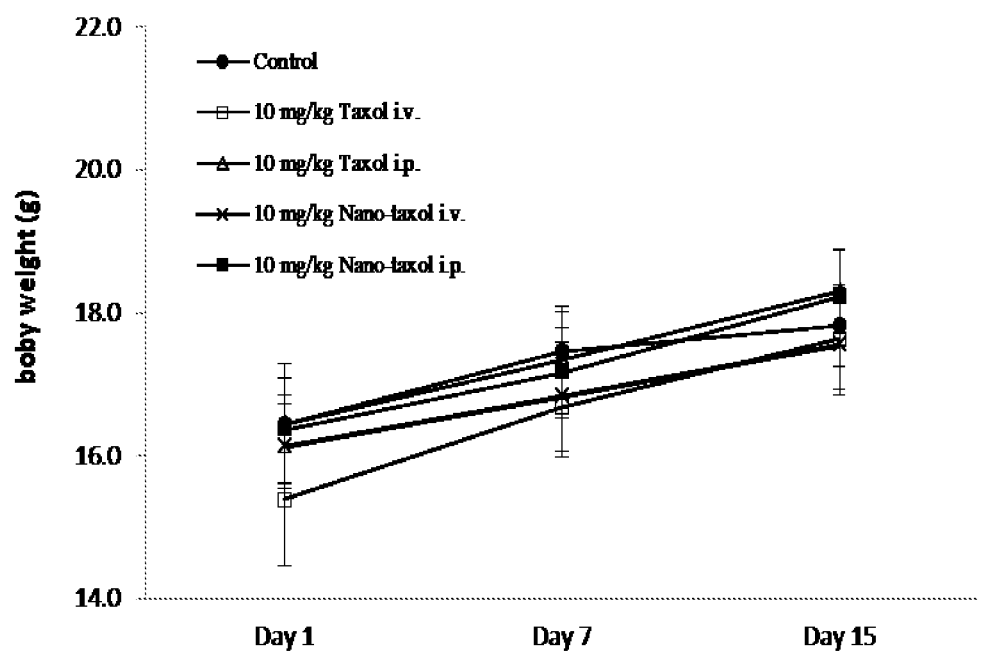
FIG. 24 shows illustrative results of the mice body weight of the animal study associated with FIG. 23A-B.

FIG. 24 shows that all treatments did not significantly alter body weight of animals.

Survival

The survival duration was 27 days in the control mice after the inoculation of $1 \times 10^5$ CT-26-luc cells (FIG. 24). Following i.v. administration of PTX at 10 mg/kg, Nano-taxol at 10 and i.p. administration of PTX at 10 mg/kg, survival duration were 27 days (FIG. 24). Following i.p. administration of 10 mg/kg Nano-taxol, survival duration was 40 days (FIG. 24). Intraperitoneal administration of 10 mg/kg Nano-taxol significantly prolonged the survival duration 13 days compared with control group ($p<0.05$).

Figure 25:
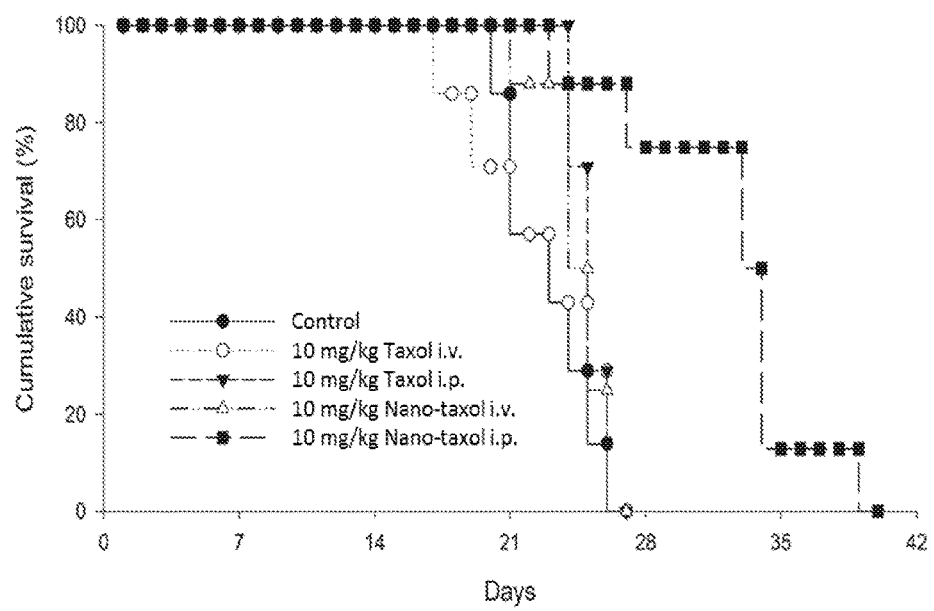
FIG. 25 shows illustrative results of the survival of the CT-26-luc i.p. injected mouse model after treatment with Nano-taxol or PTX. CT-26-luc cells ($1 \times 10^5$ cells) were inoculated into the peritoneal cavity of mice on Day 1. Saline as the vehicle control (●), 10 mg/kg PTX i.v (○), 10 mg/kg PTX i.p. (▼), 10 mg/kg Nano-taxol i.v. (Δ), 10 mg/kg Nano-taxol i.p. (■) was administered on Days 4, 6 and 8, and the survival duration was analyzed (Control and PTX group, n=7; Nano-taxol group, n=8). This survival based on FIG. 23 mice.

The median survival day of control group was 24 days. Following i.v. or i.p. administration of PTX at 10 mg/kg, median survival day was 24 and 26 days, respectively. Following i.v. or i.p. administration of Nano-taxol at 10 mg/kg, median survival day was 26 and 35 days, respectively (FIG. 25). Nano-taxol inhibited colon cancer CT-26-luc cells growth in vivo only following i.p. administration. 10 mg/kg Nano-taxol i.p. reduced tumor burden in 6 of 8 mice, but tumor eradication was not found. The response rate was 75%.

In conclusion, Nano-taxol at 10 mg/kg showed moderate antitumor activity in the colon cancer syngeneic model following intraperitoneal administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating cancer in a subject comprising administering to said subject intraperitoneally in need thereof an anti-cancer agent encapsulated in nanoparticles, wherein said nanoparticles are liposomes, and wherein said nanoparticles comprise all of hydrogenated soy phosphatidylcholine, cholesterol and d-alpha-tocopheryl polyethylene glycol succinate, and wherein said nanoparticles slowly release anti-cancer agent at a rate of 30% or less per 24 hours based on in vitro drug dissolution.

2. The method of claim 1 wherein said anti-cancer agent is selected from the group consisting of gemcitabine, idarubicin/cytarabine, etopside phosphate, gleevec, temozolomide, bortezomib, letrozole, cetuximab, bevacizumab, paclitaxel, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, Ipilimumab, RAD001, Pazopanib, FOLFIRI, BKM120, GSK1120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifarnib/gemcitabline, tootecan, and combinations thereof.

3. The method of claim 2, wherein said anti-cancer agent is paclitaxel.

4. The method of claim 1 wherein said cancer is ovarian cancer, lung cancer, liver cancer, gastric cancer, or colon cancer.

5. The method of claim 4, wherein said cancer is ovarian or colon cancer.

6. A method for treating cancer via regional delivery in a subject comprising administering intrapleurally to said subject in need thereof an anti-cancer agent encapsulated in sustained release nanoparticles, wherein said nanoparticles are liposomes, and wherein said nanoparticles comprise all of hydrogenated soy phosphatidylcholine, cholesterol and d-alpha-tocopheryl polyethylene glycol succinate wherein the anti-cancer agent nanoparticles slowly release anti-cancer agent at a rate of 30% or less per 24 hours based on in vitro drug dissolution.

7. The method of claim 6, wherein the cancer is ovarian cancer, lung cancer, liver cancer, gastric cancer, or colon cancer.

8. The method of claim 7, wherein the cancer is metastasis.

9. The method of claim 6, wherein said subject has severe adhesion in the peritoneal cavity.

10. The method of claim 6, wherein said anti-cancer agent is paclitaxel.

* * * * *